United States Patent
Park et al.

(10) Patent No.: US 12,221,638 B2
(45) Date of Patent: Feb. 11, 2025

(54) METHOD FOR PRODUCING RECOMBINANT HYALURONIDASE

(71) Applicant: ALTEOGEN Inc., Daejeon (KR)

(72) Inventors: Soon Jae Park, Daejeon (KR); Kyuwan Kim, Daejeon (KR); Sang Hoon Yun, Daejeon (KR); Jeong Soo Cho, Daejeon (KR); Kibum Park, Daejeon (KR); Minsoo Byun, Daejeon (KR); Hyung-Nam Song, Daejeon (KR); Ji-Sun Kim, Daejeon (KR); Ki Seok Nam, Daejeon (KR)

(73) Assignee: ALTEOGEN Inc., Daejeon (KR)

(*) Notice: Subject to any disclaimer, the term of this patent is extended or adjusted under 35 U.S.C. 154(b) by 0 days.

(21) Appl. No.: 17/907,538

(22) PCT Filed: Aug. 6, 2021

(86) PCT No.: PCT/KR2021/010368
§ 371 (c)(1),
(2) Date: Sep. 27, 2022

(87) PCT Pub. No.: WO2022/031093
PCT Pub. Date: Feb. 10, 2022

(65) Prior Publication Data
US 2023/0174963 A1 Jun. 8, 2023

(30) Foreign Application Priority Data
Aug. 7, 2020 (KR) .......... 10-2020-0099100

(51) Int. Cl.
*C12N 9/26* (2006.01)
(52) U.S. Cl.
CPC .... *C12N 9/2474* (2013.01); *C12Y 302/01035* (2013.01)
(58) Field of Classification Search
None
See application file for complete search history.

(56) References Cited

U.S. PATENT DOCUMENTS

| | | | |
|---|---|---|---|
| 5,721,348 A | 2/1998 | Primakoff et al. |
| 5,854,046 A | 12/1998 | Au-Young et al. |
| 7,767,429 B2 | 8/2010 | Bookbinder et al. |
| 8,105,586 B2 | 1/2012 | Bookbinder et al. |
| 8,202,517 B2 | 6/2012 | Bookbinder et al. |
| 8,257,699 B2 | 9/2012 | Bookbinder et al. |
| 8,288,142 B2 | 10/2012 | Uvarkina et al. |
| 8,431,124 B2 | 4/2013 | Bookbinder et al. |
| 8,580,252 B2 | 11/2013 | Bookbinder et al. |
| 8,927,249 B2 | 1/2015 | Wei et al. |
| 9,211,315 B2 | 12/2015 | Bookbinder et al. |
| 9,284,543 B2 | 3/2016 | Wei et al. |
| 9,447,401 B2 | 9/2016 | Wei et al. |
| 10,286,044 B2 | 5/2019 | Bookbinder et al. |
| 10,328,130 B2 | 6/2019 | Frost et al. |
| 10,865,400 B2 | 12/2020 | Wei et al. |
| 10,918,736 B2 | 2/2021 | Kim et al. |
| 11,041,149 B2 | 6/2021 | Wei et al. |
| 11,066,656 B2 | 7/2021 | Wei et al. |
| 2006/0104968 A1 | 5/2006 | Bookbinder et al. |
| 2010/0003238 A1 | 1/2010 | Frost et al. |
| 2010/0143457 A1 | 6/2010 | Wei et al. |
| 2011/0044977 A1 | 2/2011 | Adler |
| 2012/0148535 A1 | 6/2012 | Carrio et al. |
| 2013/0101577 A9 | 4/2013 | Wei et al. |
| 2013/0302275 A1 | 11/2013 | Wei et al. |
| 2014/0199282 A1 | 7/2014 | Bookbinder et al. |
| 2015/0001529 A1 | 1/2015 | Kurokawa |
| 2015/0010529 A1 | 1/2015 | Wei |
| 2015/0165059 A1 | 6/2015 | Bookbinder et al. |
| 2016/0362670 A1 | 12/2016 | Wei et al. |
| 2017/0089914 A1 | 3/2017 | Loo et al. |
| 2017/0218069 A1 | 8/2017 | Rosengren et al. |
| 2017/0218382 A1 | 8/2017 | Kondo |
| 2018/0044419 A9 | 2/2018 | Rosengren et al. |
| 2018/0185506 A1 | 7/2018 | Bookbinder et al. |
| 2018/0250397 A1 | 9/2018 | Benyunes et al. |
| 2019/0046657 A1 | 2/2019 | Kim et al. |
| 2021/0155913 A1 | 5/2021 | Park |
| 2021/0363270 A1 | 11/2021 | Park et al. |
| 2022/0089738 A1 | 3/2022 | Krishnamachari et al. |
| 2022/0289864 A1 | 9/2022 | Park et al. |

(Continued)

FOREIGN PATENT DOCUMENTS

| | | |
|---|---|---|
| CN | 101970650 A | 2/2011 |
| CN | 102065886 A | 5/2011 |
| CN | 102307993 A | 1/2012 |
| CN | 103173474 A | 6/2013 |
| CN | 104244968 A | 12/2014 |
| CN | 110494450 A | 11/2019 |
| CN | 111971387 A | 11/2020 |
| CO | 2021011944 A2 | 9/2021 |
| EA | 22752 B1 | 2/2016 |
| EP | 2662090 A1 | 11/2013 |
| EP | 3037529 A1 | 6/2016 |
| EP | 2797622 B1 | 10/2016 |
| EP | 3130347 B1 | 9/2019 |
| EP | 3636752 A1 | 4/2020 |

(Continued)

OTHER PUBLICATIONS

Chica et al. Curr Opin Biotechnol. Aug. 2005;16(4):378-84. (Year: 2005).*

(Continued)

*Primary Examiner* — Christian L Fronda
(74) *Attorney, Agent, or Firm* — Sughrue Mion, PLLC

(57) ABSTRACT

Disclosed is a method for producing hyaluronidase or a variant thereof. Specifically, the method is capable of changing the N-glycan levels under culture conditions including a controlled concentration of glucose in the culture medium and a decreased culture temperature for a specific culture time period, thereby increasing the specific activity by 10% or more and improving the quality and production yield.

15 Claims, 20 Drawing Sheets

Specification includes a Sequence Listing.

(56) References Cited

U.S. PATENT DOCUMENTS

| | | |
|---|---|---|
| 2023/0174963 A1 | 6/2023 | Park et al. |
| 2023/0250408 A1 | 8/2023 | Park et al. |
| 2023/0365692 A1 | 11/2023 | Krishnamachari et al. |

FOREIGN PATENT DOCUMENTS

| | | |
|---|---|---|
| EP | 3785701 A1 | 3/2021 |
| JP | 2009515521 A | 4/2009 |
| JP | 2011512844 A | 4/2011 |
| JP | 2015504666 A | 2/2015 |
| JP | 2020500863 A | 1/2020 |
| JP | 7166478 B2 | 7/2022 |
| KR | 1020100135291 A | 12/2010 |
| KR | 20120094493 A | 8/2012 |
| KR | 1020120105426 A | 9/2012 |
| KR | 101233457 B1 | 2/2013 |
| KR | 1020130116386 A | 10/2013 |
| KR | 101363658 B1 | 2/2014 |
| KR | 1020140021046 A | 2/2014 |
| KR | 101493644 B1 | 2/2015 |
| KR | 101546563 B1 | 8/2015 |
| KR | 1020160052812 A | 5/2016 |
| KR | 101647932 B1 | 8/2016 |
| KR | 10-2017-0065032 A | 6/2017 |
| KR | 101874401 B1 | 7/2018 |
| KR | 1020200017538 A | 2/2020 |
| KR | 1020200130451 A | 11/2020 |
| KR | 10-2021-0023798 A | 3/2021 |
| KR | 10-2022-0069045 A | 5/2022 |
| TW | 201534726 A | 9/2015 |
| WO | 2004078140 A2 | 9/2004 |
| WO | 2007064437 A2 | 6/2007 |
| WO | 2009065507 A2 | 5/2009 |
| WO | 2009117085 A1 | 9/2009 |
| WO | 2009128917 A2 | 10/2009 |
| WO | 2010077297 A1 | 7/2010 |
| WO | 2011012637 A2 | 2/2011 |
| WO | 2011029892 A2 | 3/2011 |
| WO | 2012135408 A | 4/2012 |
| WO | 2013102144 A2 | 7/2013 |
| WO | 2015003167 A1 | 1/2015 |
| WO | 2015071366 A1 | 5/2015 |
| WO | 2016033555 A1 | 3/2016 |
| WO | 2017004706 A1 | 1/2017 |
| WO | 2017079150 A1 | 5/2017 |
| WO | 2017131496 A1 | 8/2017 |
| WO | 2018102372 A1 | 6/2018 |
| WO | 2018204368 | 8/2018 |
| WO | 2018183928 A1 | 10/2018 |
| WO | 2018222722 A2 | 12/2018 |
| WO | 2019222435 A1 | 11/2019 |
| WO | 2020022791 A1 | 1/2020 |
| WO | 2020197230 A1 | 1/2020 |
| WO | 2020172621 A1 | 8/2020 |
| WO | 2021150079 A1 | 7/2021 |
| WO | 2022031093 A1 | 2/2022 |
| WO | 2023075506 A1 | 5/2023 |

OTHER PUBLICATIONS

Singh et al. Curr Protein Pept Sci. 2017, 18, 1-11 (Year: 2017).*
Arming, S., et al., "In vitro mutagenesis of PH-20 hyaluronidase from human sperm", Eur. J. Biochem, 1997, pp. 810-814, vol. 247.
Bookbinder, L.H., et al., "A recombinant human enzyme for enhanced interstitial transport of therapeutics", Journal of Controlled Release, 2006, pp. 230-241, vol. 114, Publisher: Science Direct.
Borys, M.C., et al., "Culture pH Affects Expression Rates and Glycosylation of Recombinant Mouse Placental Lactogen Proteins by Chinese Hamster Ovary (CHO) Cells", Biotechnology, 1993, pp. 720-724, vol. 11, Publisher: Nature Publishing Group.
Borys, M.C., et al., "Ammonia Affects the Glycosylation Patterns of Recombinant Mouse Placental Lactogen-I by Chinese Hamster Overy Cells in a pH-Dependent Manner", Biotechnology and Bioengineering, 1994, pp. 505-514, vol. 43, Publisher: John Wiley & Sons, Inc.
Chen, K-J, et al., "Constitutive expression of recombinant human hyaluronidase PH20 by Pichia pastoris", Journal of Bioscience and Bioengineering, 2016, pp. 673-678, vol. 122, Publisher: Elsevier.
Clark, K.J.R., et al., "Temperature Effects on Product-Quality-Related Enzymes in Batch CHO Cell Cultures Producing Recombinant tPA", Biotechnol. Prog., 2004, pp. 1888-1892, vol. 20, Publisher: American Chemical Society.
Clement, W.A., et al., "The use of hyaluronidase in nasal infiltration: prospective randomized controlled pilot study", The Journal of Laryngology & Otology, 2003, pp. 614-618, vol. 117.
Frost, G.I., "Recombinant human hyaluronidase (rHuPH20): an enabling platform for subcutaneous drug and fluid administration", Expert Opin Drug Deliv, 2007, pp. 427-440, vol. 4.
Harb, G., et al., "Safety and pharmakokinetics of subcutaneous ceftriaxone administered with or without recombinant human hyaluronidase (rHuPH20) versus intravenous ceftriaxone administration in adult volunteers", Current Medical Research & Opinion, 2010, pp. 279-288, vol. 26, No. 2, Publisher: CMRO.
Harris, R.J., et al., "Commercial Manufacturing Scale Formulation and Analytical Characterization of Therapeutic Recombinant Antibodies", Drug Development Research, 2004, pp. 137-154, vol. 61.
Krantz, E.M., "Low-Dose Intramuscular Ketamine and Hyaluronidase for Induction of Anaesthesia in Non-Pemedicated Children", S.A. Med. J., 1980, pp. 161-162, vol. 58, No. 4.
Locke, K.W., et al., "ENHANZE drug delivery technology: a novel approach to subcutaneous administration using recombinant human hyaluronidase PH20", Drug Delivery, 2019, pp. 98-106; DOI:10.1080/10717544.2018.1551442, vol. 26, No. 1, Publisher: Taylor & Francis.
Muchmore, D.B., et al., "Accelerating and Improving the Consistency of Rapid-Acting Analog Insulin Absorption and Action for Both Subcutaneous Injection and Continuous Subcutaneous Infusion Using Recombinant Human Hyaluronidase", Journal of Diabetes Sciene and Technology, 2012, pp. 764-772, vol. 6, No. 4, Publisher: Diabetes Technology Society.
Restelli, V., et al., "The Effect of Dissolved Oxygen on the Production and the Glycosylation Profile of Recombinant Human Erythropoietin Produced From CHO Cells", Biotechnol Bioeng, 2006, pp. 481-494, vol. 94.
Schilling, S., et al., "Heterologous Expression and Characterization of Human Glutaminy Cyclase: Evidence for a Disulfide Bond with Importance for Catalytic Activity", Biochemistry, 2002, pp. 10849-10857, vol. 41, Publisher: American Chemical Society.
Tachibana, H., et al., "Changes of monosacharide availability of human hybridoma lead to alteration of biological properties of human monoclonal antibody", Cytotechnology, 1994, pp. 151-157, vol. 16, Publisher: Kluwer Academic Publishers.
Thomas, J.R., et al., "The INFUSE-Morphine Study: Use of Recombinant Human Hyaluronidase (rHuPH20) to Enhance the Absorption of Subcutaneously Administered Morphine in Patients with Advanced Illness", Journal of Pain and Symptom Management, 2009, vol. 38, No. 5663-672, Publisher: Elsevier.
Wasserman, R.L., "Overview of recombinant human hyaluronidase-faciliated subcutaneous infusion of IgG in primary immunodeficiencies", Immunotherapy, 2014, pp. 553-567, vol. 6, No. 5, Publisher: Future Medicine.
Office Action issued on Sep. 5, 2022 in counterpart Taiwan Patent Application 110130965, Sep. 5, 2022.
English Translation of Office Action issued on Sep. 5, 2022 in counterpart Taiwan Patent Application 110130965, Sep. 5, 2022.
Office Action Issued in Japanese Patent Application No. 2022559471 on Oct. 11, 2023.
English Translation of Office Action Issued in Japanese Patent Application No. 2022559471 on Oct. 11, 2023.
AU2020248612—Examination Report No. 2 mailed on Oct. 25, 2023, 3 pages.
CA3, 131,052—Office Action mailed on May 6, 2024, 5 pages.
EP20776465.5—Extended European search report mailed on Feb. 11, 2022, 15 pages.
KR20210103530—Request for the Submission of an Opinion mailed on Sep. 19, 2023, 7 pages.

(56) References Cited

OTHER PUBLICATIONS

RU2022125351—Office Action mailed on Nov. 2, 2023, 15 pages.
International Search Report and Written Opinion dated Nov. 18, 2021 in International Application No. PCT/KR2021/010368, p. 17.
RU2021132331—Decision of grant mailed on Nov. 3, 2023, 16 pages.
AU2020248612—Notice of Acceptance mailed on Sep. 21, 2023, 4 pages.
JP2022211105—Decision of Dismissal of Amendment mailed on May 14, 2024, 4 pages.
JP2021567961—Office Action mailed on Jul. 2, 2024, 6 pages.
CN202180003323.4—Office Action mailed on Jul. 10, 2024, 12 pages.
Tavares, A. et al., "Inhibition of the checkpoint protein PD-1 by the therapeutic antibody pembrolizumab outlined by quantum chemistry", Scientific Reports, vol. 8, Issue 1840, pp. 1-13.
CONC20210012380—Office Action mailed on Jan. 11, 2024, 16 pages.
EA202192588—Office Action mailed on Sep. 29, 2023, 8 pages.
IDP00202108509—Office Action mailed on Sep. 27, 2023, 4 pages.
PA93644-01—Search Report mailed on Mar. 29, 2022, 8 pages.
VN1-2021-06635—Office Action mailed on Feb. 26, 2024, 3 pages.
U.S. Appl. No. 16/628,258—Notice of Allowance mailed on Jul. 16, 2024, 8 pages.
U.S. Appl. No. 17/608,729—Requirement for Restriction/Election mailed on May 14, 2024, 5 pages.
Appendix A Sequence Alignment, 2024.
Office Action dated Jul. 9, 2021 in Taiwanese Patent Application No. 109119328.
Chan et al., "Therapeutic antibodies for autoimmunity and inflammation", Nature Reviews Immunology, vol. 10, May 2010, pp. 301-316.
Alley et al., "Long-Term Overall Survival for Patients with Malignant Pleural Mesothelioma on Pembrolizumab Enrolled in KEYNOTE-028", Journal of Thoracic Oncology, Abstract No. OA13.03, 2018, vol. 12, No. 1S, p. 1 (S294).
Liming Liu, "Pharmacokinetics of monoclonal antibodies and Fc-fusion proteins", Protein Cell, 2018, vol. 9, No. 1, pp. 15-32.
U.S. Appl. No. 17/052,952—Non-Final Office Action mailed on Dec. 12, 2023, 32 pages.
International Search Report and Written Opinion mailed Jul. 29, 2021 for International Patent Application No. PCT/KR2021/000943 filed Mar. 24, 2020 (21 pages).
International Search Report and Written Opinion mailed Jun. 30, 2020 for International Patent Application No. PCT/KR2020/003975 filed Mar. 24, 2020 (23 pages).
International Search Report and Written Opinion mailed Oct. 29, 2019 for PCT Application No. PCT/KR2019/009215 filed Jul. 25, 2019 (21 pages).
Lin et al. "Molecular cloning of the human and monkey sperm surface protein PH-20", Proc. Natl. Acad. Sci. Nov. 1993, vol. 90, p. 10071-10075.
Mcatee, C., et al., "Emerging roles for hyaluronidase in cancer metastasis and therapy", "Advances in cancer research", 2014, vol. 123, pp. 1-34.
Muller et al., "Spliceosomal peptide P140 for immunotherapy of systemic lupus erythematosus", Arthritis & Rheumatism, Dec. 2008, vol. 58, Nb. 12, pp. 3873-3883.
Hyaluronidase PH-20 (Macaca nemestrina) NCBI Reference Sequence: XP011728213.1, Apr. 24, 2018, p. 2.
NCBI Reference Sequence: NP 001166492.1, hyaluronidase PH-20 precursor [Cavia porcelius], Jun. 21, 2021, p. 2.
NCBI Reference Sequence: NP 001166492.1, hyaluronidase PH-20 precursor [Cavia porcelius], Jun. 19, 2020, p. 2.
"PH-20 (*Homo sapiens*)", NCBI Genbank Accession No. AAC60607.2, Jun. 5, 2000, p. 1.
Wang et al., "Antibody structure, instability, and formulation,"Journal of pharmaceutical sciences., Jan. 2007, vol. 96, Nb.1, pp. 1-26.
FROST and Stern, "A microtiter-based assay for hyaluronidase activity not requiring specialized reagents", "Analytical Biochemistry", 1997, vol. 251, pp. 263-269.
Markovic-Housley et al., "Crystal structure of hyaluronidase, a major allergen of bee venom", "Structure", Oct. 2000, vol. 8, , pp. 1025-1035.
Messina et al., "Identification and characterization of a bacterial hyaluronidase and its production in recombinant form", "FEBS Letters", 2016, vol. 590, Issue 14, pp. 2180-2189.
STERN and CSOKA, "Mammalian Hyaluronidases", "Glycoforum", 2000, vol. 4, pp. 1-6.
Lafaro et al., "The Paradoxical Web of Pancreatic Cancer Tumor Microenvironment", The American journal of pathology, vol. 189, No. 1, pp. 44-57.
Philo et al., "A Critical Review of Methods for Size Characterization of Non-Particulate Protein Aggregates," U.S. Cur. Pharm. Biotech., 2009, vol. 10, 359-372.
Takahashi, T et al., "A fluorimetric Morgan-Elson assay method for hyaluronidase activity," Anal. Biochem., 2003, vol. 322, 257-263.
Office Action issued in Australian Patent Application No. 2020248612 on Nov. 8, 2022, p. 3.
Office Action issued in Canadian Patent Application No. 3131052 on Oct. 19, 2022, p. 6.
U.S. Appl. No. 16/628,258—Final Rejection mailed on Mar. 12, 2024, 9 pages.
U.S. Appl. No. 16/628,258—Non-Final Office Action mailed on Aug. 30, 2023, 13 pages.
U.S. Appl. No. 16/628,258—Requirement for Restriction/Election mailed on Mar. 23, 2023, 9 pages.
CA3137324—Office Action mailed on May 6, 2024, 6 pages.
Schon, A., et al., "Denatured state aggregation parameters derived from concentration dependence of protein stability", Analytical Biochemistry, 2015, pp. 45-50, vol. 488, Publisher: Elsevier.
STERN and Jedrzejas, "The Hyaluronidases: Their Genomics, Structures, and Mechanisms of Action", "Chern Rev.", 2006, pp. 818-839, vol. 106, No. 3 with supplemental.
Chao, K., et al., "Structure of Human Hyaluronidase-1, a Hyaluronan Hydrolyzing Enzyme Involved in Tumor Growth and Angiogenesis", Biochernis! 2007, pp. 6911-6920, vol. 46.
EESR Issued in counterpart European Patent Application No. 21743774.8 on Jan. 4, 2023.
Broun, P., et al., "Catalytic Plasticity of Fatty Acid Modification Enzymes Underlying Chemical Diversity of Plant D Lipids", SCIENCE, 1998, pp. 1315-1317, vol. 282, No. 13, Publisher: www.sciencemag.org.
Hiromoto, Y., et al., "An Activity-Straining Method on Filtration Paper Enables High-Throughput Screening of Temperature-Sensitive and Inactive Mutations of Rice -Amylase for Improvement of Rice Grain Quality", Plant and Cell Physiology, 2017, pp. 658-667, vol. 58, No. 4, Publisher: Japanese Society of Plant Physiologists.
Office Action issued on Dec. 2, 2022 in counterpart Canadian Patent Application No. 2137324, p. 4.
Office Action issued on Oct. 17, 2022 in counterpart Russian Patent Application No. 2021132331, p. 18.
Seffernick, J.L., et al., "Melamine Deaminase and Atrazine Chlorohydrolase: 98 Percent Identical but Functionally Different", Journal of Bacteriology, 201, pp. 2405-2410, vol. 183, No. 8, Publisher: American Society for Microbiology.
Whisstock, J.D., et al., "Prediction of protein function from protein sequence and structure", Quarterly Reviews of Biophysics, 2003, pp. 307-340, vol. 36, No. 3, Publisher: Cambridge University Press.
Pakula, A., et al., "Genetic Analysis of Protein Stability and Function", Annu. Rev. Genet., 1898, , vol. 23, pp. 289-310.
Witkowski, A., et al., "Conversion of a Beta-Ketoacyl Synthase to a Malonyl Decarboxylase by Replacement of the Active-Site Cysteine with Glutamine", Biochemistry, 1999, vol. 38, Publisher: American Chemical Society, Page(s) 11643-11650.
"GenBank: AAC6067.2, PH-20 (*Homo sapiens*)", NCBI, Jun. 5, 2000, p. 2.
International Search Report dated Feb. 2, 2023 in International Application No. PCT/KR2022/016709, p. 14.

(56) References Cited

OTHER PUBLICATIONS

Strickley et al., "A review of formulations of commercially available antibodies", Journal of Pharmaceutical Sciences, 2021, vol. 110, pp. 2590-2608.
Zarrintaj et al.,"Poloxamer: A versatile tri-block copolymer for biomedical applications", Acta Biomaterialia, 2020, vol. 110, pp. 37-67.
KR1020210103530—Written Decision on Registration mailed on Dec. 15, 2023, 6 pages.
JP2022559471—Final Notification of Reasons forRefusal mailed on Mar. 19, 2024, 8 pages.
CN202180030097.9—First Office Action mailed on Jan. 6, 2024, 19 pages.
CA3173310—Office action mailed on Dec. 20, 2023, 5 pages.
CN201980023392.4—Second Office Action mailed on Feb. 8, 2024, 8 pages.
NCBI Reference Sequence, hyaluronidase PH-20 precursor [Cavia porcelius], NP_001166492.1, Jun. 21, 2021 p. 2 (downloaded Aug. 24, 2023).
Opposition dated Jul. 5, 2022 by Asociacion de Laboratorios Farmaceuticos (ALAFAR) Against Ecuadorian Application No. SENADI-2021-70640, p. 3.
Opposition filed Jan. 13, 2022 by Laboratorios Legrand S.A. against Columbian Patent Application No. NC2021/0012380, p. 21.
CN202310416462.0—First Office Action mailed on Mar. 5, 2024, 8 pages.
CN202080003052.8—Second Office Action mailed on Mar. 2, 2024, 11 pages.
CN202080003052.8—First Office Action mailed on Jun. 27, 2023, 12 pages.
JP2023026863—Notice of Reasons for Refusal mailed on Mar. 12, 2024, 10 pages.
Kreidieh, F., et al., "Overview, Prevention and Management of Chemotherapy Extravasation", "World Journal of Clinical Oncology", Feb. 10, 2016, pp. 87-97, vol. 7, No. 1.
Hofinger, E., et al., "Kinetics of Hyal-1 and PH-20 Hyaluronidases: Comparison of Minimal Substrates and Analysis of the Transglycosylation Reaction", "Glycobiology", 2007, pp. 963-971, vol. 17, No. 9.
Chen, K., et al., "Constitutive Expression of Recombinant Human Hyaluronidase PH20 by Pichia Pastoris", "Journal of Bioscience and Bioengineering", 2016, pp. 1-6.
Borders, C., et al., "Purification and Partiai Characterization of Tes ar Hyaluronidase", The Journal of Biolog Chemi 1968, vol. 243, No. 13, p. 3756-3762.
Shpilberg, O., et al., "Subcutaneous administration of rituximab (MabThera) and trastuzumab (Herceptin) using D hyaluronidase", Britich Journal of Cancer, 2013, vol. 109, p. 1556-1561.
Bittner, B., et al., "Subcutaneous Administration of Biotherapeutics - An Overview of Current Challenges and D Opportunities", BioDrugs, 2018, vol. 32, Publisher: CrossMark, p. 425-440.
Opposition by Laboratorios Legrand S.A. Against Columbian Patent Application NC20210012380 with English Translation Oct. 20, 2021, p. 21.
Office Action issued in Saudia Arabia Patent Application No. 521430398 with English Translation on Feb. 25, 2023, p. 11.
Office Action issued in Chile Patent Application No. 202102464 with English Translation on May 4, 2023, p. 23.
Opposition filed against Ecuador Patent Application SENADI-2021-70640 with English Translation on Feb. 14, 2022, p. 217.
Office Action issued in Korean Patent Application No. 20227016935 on Aug. 28, 2022.
Office Action issued in Japanese Patent Application No. 2020569741 on Aug. 23, 2022, 5 pages.
Office Action issued in Georgian Patent Application No. AP202015767 with English Translation on Apr. 3, 2023, p. 9.
CN201980023392.4—Decision of Final Rejection mailed on May 17, 2024, 10 pages.
CA3,093,885—Office Action mailed on Jun. 3, 2024, 4 pages.
JP2022-211105—Decision of Rejection mailed on May 14, 2024, 3 pages.
H. Johansen, et al., "High-level production of fully active human alpha 1-antitrypsin in *Escherichia coli*." Mol. Biol. Med. (1987) vol. 4, pp. 291-305.
J.H. Dunham, et al., "GPR37 Surface Expression Enhancement via N-Terminal Truncation or Protein-Protein Interactions", Biochemistry (2009) 48, pp. 10286-10297.
M. Wei, et al., "N-terminal truncations on L1 proteins of human papillomaviruses promote their soluble expression in Escherichia coli and self-assembly in vitro", Emerging Microbes & Infections (2018) vol. 7, p. 160.
M. F. Meyer, et al., "The soluble hyaluronidase from bull testes is a fragment of the membrane-bound PH-20 enzyme", FEBS letter (1997) vol. 413, pp. 385-388.
International Search Report and Written Opinion dated Sep. 21, 2023 in International Application No. PCT/ KR2023/008621, p. 15.
AU2021320569—Examination Report No. 1 mailed on Apr. 30, 2024, 3 pages.
CN2021800300979—First Office Action mailed on Jan. 6, 2024, 18 pages.
MX/a/2020/009824—Office Action mailed on Jun. 10, 2024, 16 pages.
TW111145281—First Office Action mailed on May 29, 2024, 16 pages.
TW111128188—First Office Action mailed on May 29, 2024, 24 pages.
TW110102662—Office Action mailed on May 3, 2024, 22 pages.
TW111136059—Office Action mailed on May 3, 2024, 20 pages.
JP2022211105—Notice of Reasons for Refusal mailed on Nov. 14, 2023, 17 pages.
CN201980023392.4—First Office Action mailed on Jun. 17, 2023, 9 pages.
KR20207002955—Written Decision on Registration mailed on Aug. 25, 2020, 16 pages.
JP2020500863—Notice of Reasons for Refusal mailed on Jan. 25, 2022, 7 pages.
JP2020500863—Notice of Reasons for Refusal mailed on May 24, 2022, 6 pages.
JP2020500863—Notice of Reasons for Refusal mailed on Jun. 15, 2021, 12 pages.
EP19827585—Supplementary European search report mailed on Mar. 31, 2021, 9 pages.
JP2022211105—Decision of Rejection mailed on May 14, 2024, 2 pages.
CA3,093,885—Examiner Requisition mailed on Sep. 1, 2021, 4 pages.
CA3,093,885—Examiner Requisition mailed on Oct. 3, 2022, 6 pages.
AU2019311658—Examination Report No. 1 mailed on Jun. 17, 2022, 3 pages.
AU2019311658—Notice of Acceptance mailed on Oct. 11, 2022, 3 pages.
Bazhenova et al., Cancer Research, vol. 77, No. 13, suppl. Abstract No. CT032.
U.S. Appl. No. 17/052,952—Non-Final Office Action mailed on Jun. 13, 2024, 20 pages.
KR20227013211—Request for the Submission of an Opinion mailed on Apr. 26, 2024, 7 pages.
CN202180003323.4—First Office Action mailed on Nov. 27, 2023, 14 pages.
EP21743774—Supplementary European search report mailed on Jan. 4, 2023, 20 pages.
JP2021567961—Decision of Rejection mailed on Nov. 14, 2023, 8 pages.
JP2021567961—Notice of Reasons for Refusal mailed on Apr. 11, 2023, 6 pages.
AU2021211348—Examination Report No. 1 mailed on Mar. 17, 2023, 3 pages.
AU2021211348—Examination Report No. 2 mailed on Jul. 11, 2023, 5 pages.
AU2021211348—Notice of Acceptance mailed on Sep. 21, 2023, 4 pages.

(56) References Cited

OTHER PUBLICATIONS

CA3,137,324—Examiner Requisition mailed on Dec. 2, 2022, 4 pages.
CA3,137,324—Examiner Requisition mailed on May 6, 2024, 6 pages.
KR20207030248—Written Decision on Registration mailed on Dec. 22, 2023, 5 pages.
KR20207030248—Notice of Final Rejection mailed on Jul. 27, 2023, 6 pages.
KR20207030248—Request for the Submission of an Opinion mailed on Aug. 28, 2022, 14 pages.
KR20227016935—Written Decision on Registration mailed on Dec. 21, 2022, 6 pages.
JP2022068166—Notice of Reasons for Refusal mailed on Jun. 21, 2022, 8 pages.
JP2022068166—Decision to Grant a Patent mailed on Oct. 4, 2022, 5 pages.
JP2020569741—Notice of Reasons for Refusal mailed on Nov. 16, 2021, 8 pages.
JP2020569741—Decision to Grant a Patent mailed on May 16, 2023, 5 pages.
CN202310416462.0—Notification of grant of patent right for invention mailed on May 16, 2024, 3 pages.
AU2020248612—Examination Report No. 3 mailed on Nov. 8, 2023, 2 pages.

\* cited by examiner

[Fig. 1]
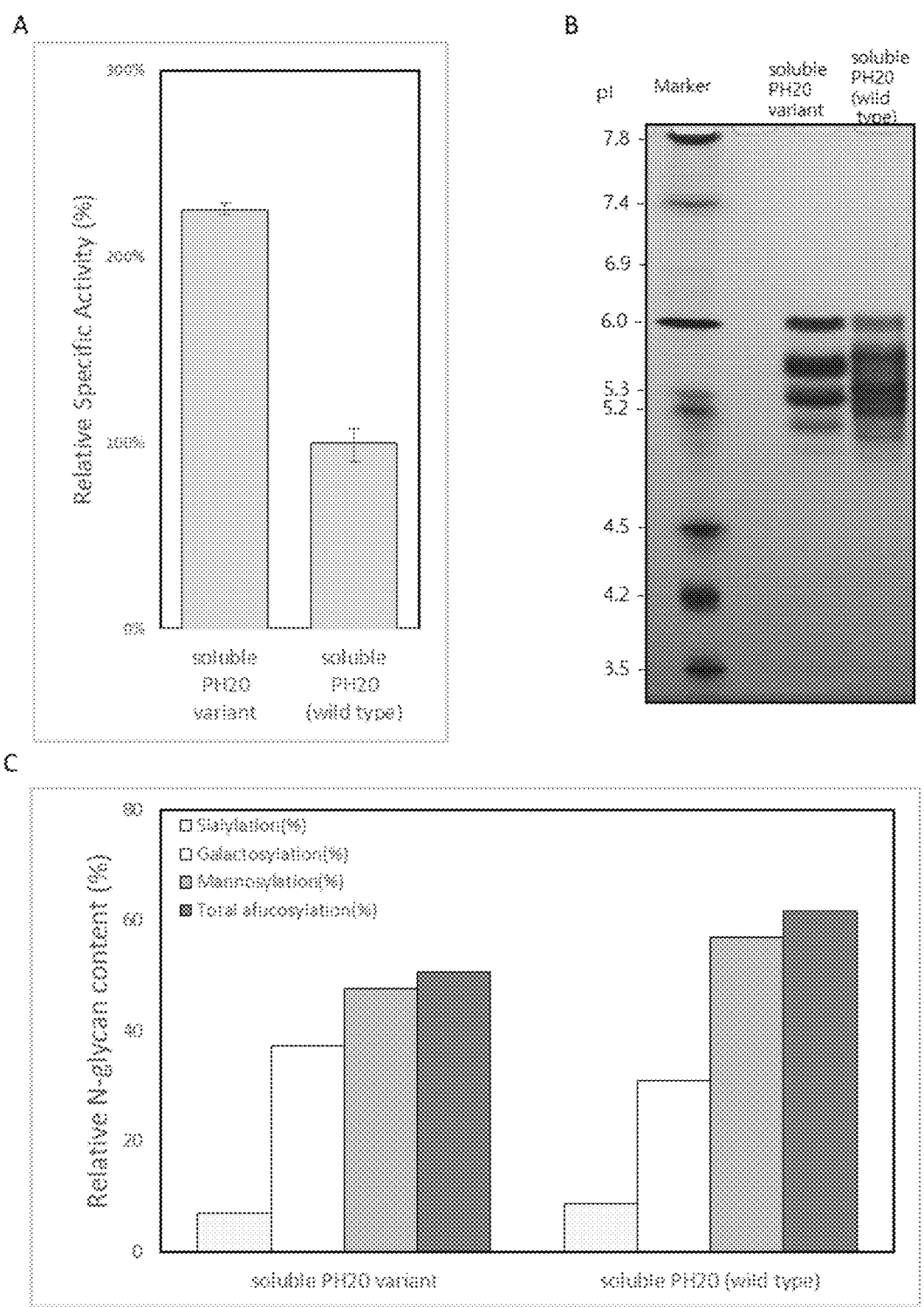

[Fig. 2]
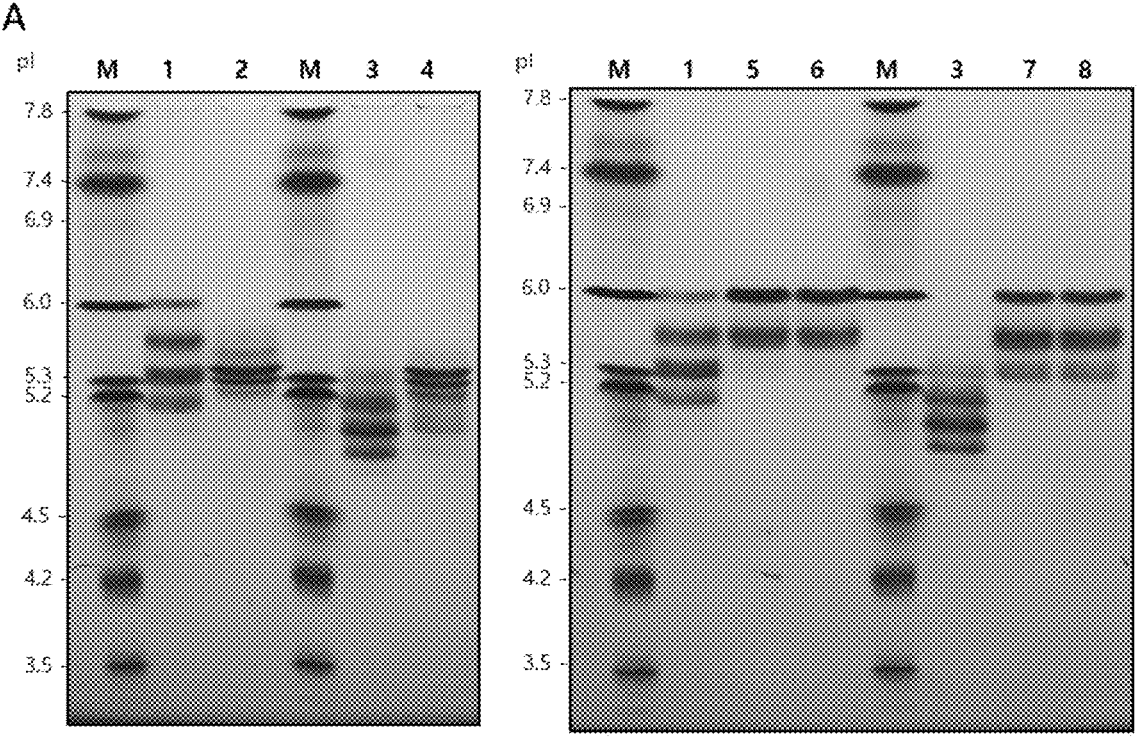
Lane M  Marker
Lane 1  Fraction 1: No treatment
Lane 2  Fraction 1: PNGase F
Lane 3  Fraction 2: No treatment
Lane 4  Fraction 2: PNGase F
Lane 5  Fraction 1: Sialidase A
Lane 6  Fraction 1: Sialidase A
        + Galactosidase
Lane 7  Fraction 2: Sialidase A
Lane 8  Fraction 2: Sialidase A
        + Galactosidase 【Fig. 2】 (continued)
B
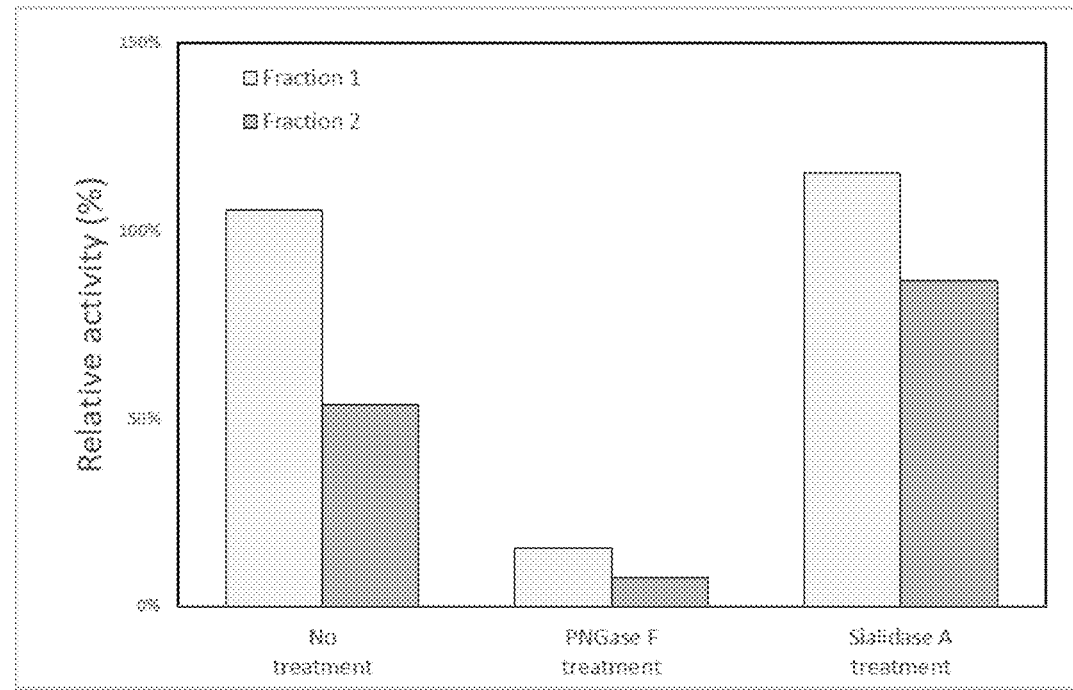
C
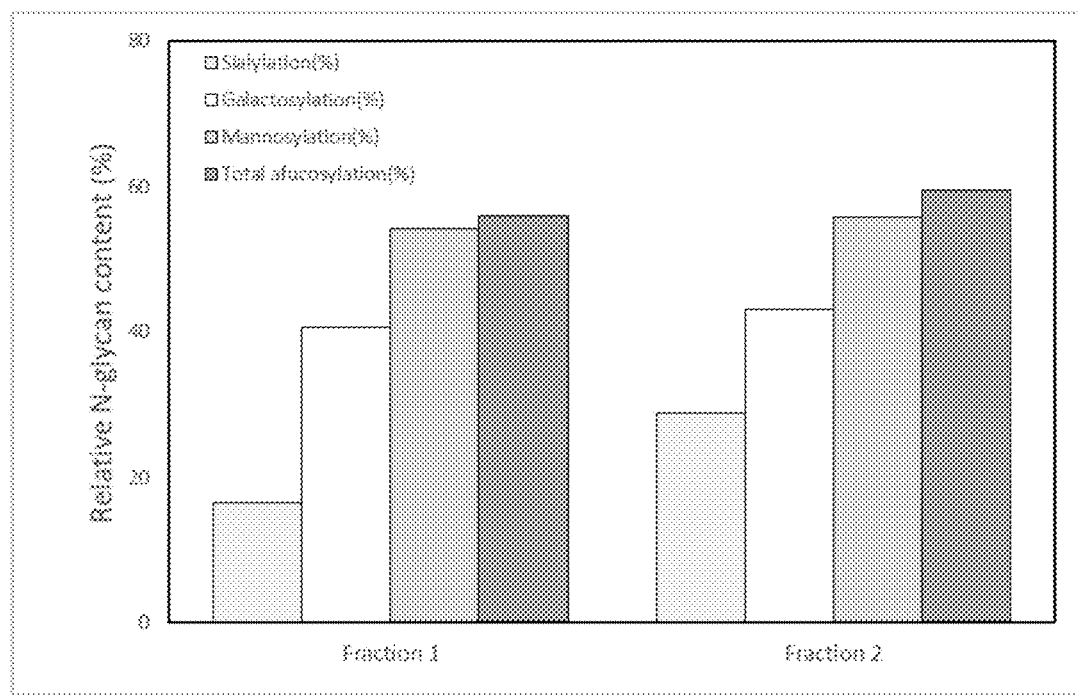

[Fig. 3]
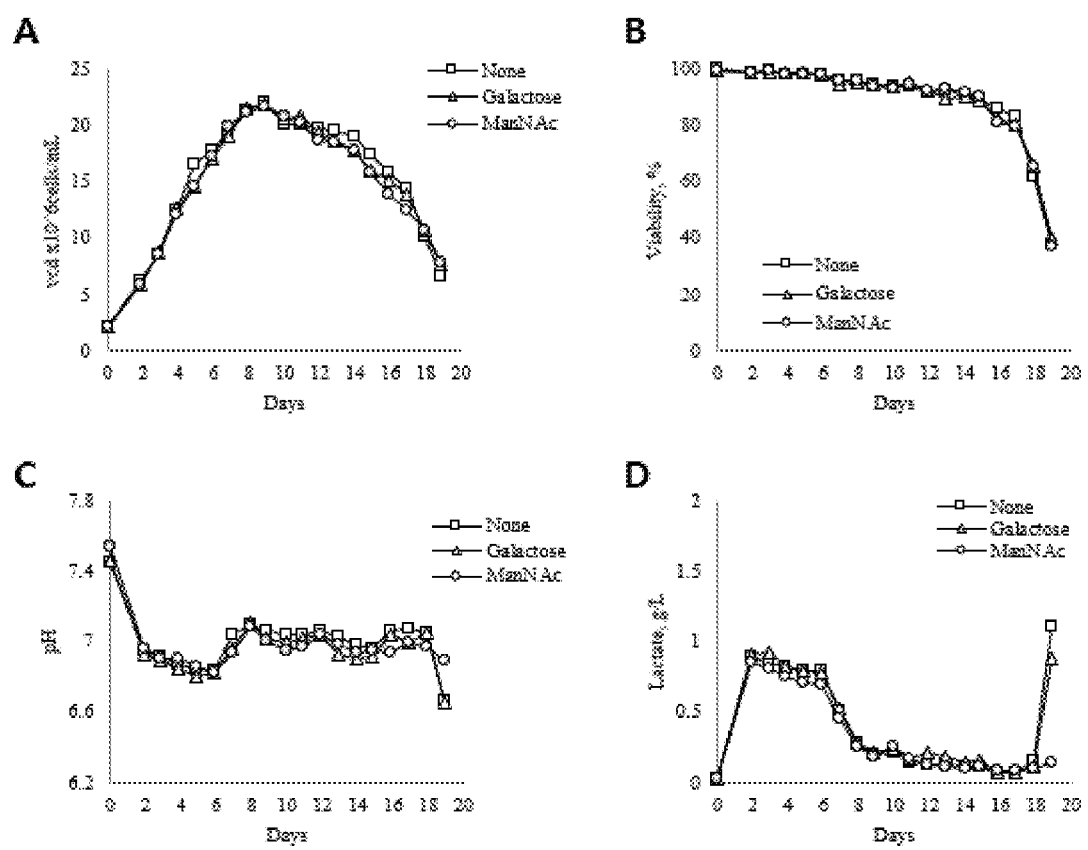

[Fig. 4]
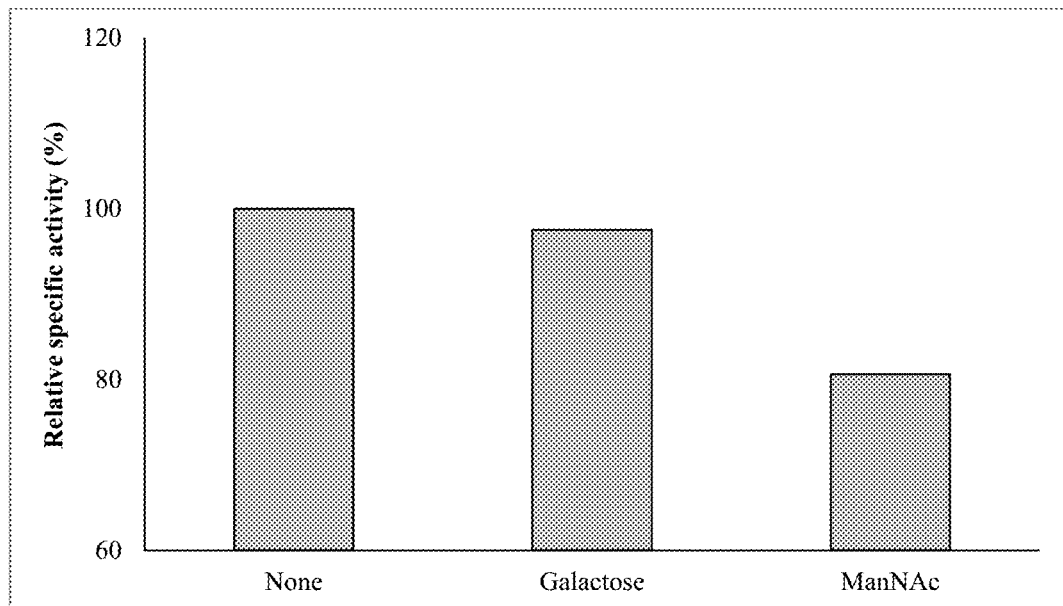
[Fig. 5]
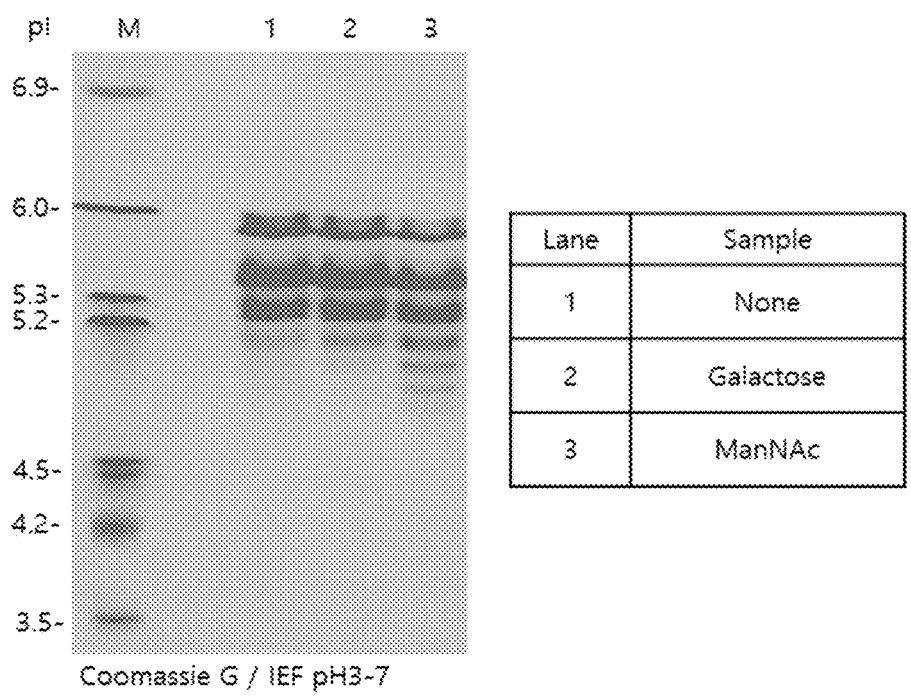
| Lane | Sample |
|------|----------|
| 1 | None |
| 2 | Galactose |
| 3 | ManNAc |

[Fig. 6]

| N-Glycan pattern | None | Galactose | ManNAc |
|---|---|---|---|
| Galactosylation (%) | 26.3 | 34.6 | 21.7 |
| Sialylation (%) | 7.4 | 9.1 | 11.4 |
| Mannosylation (%) | 46.8 | 45.8 | 51.7 |
| Total afucosylation (%) | 49.7 | 51.6 | 55.1 |
| Afucosylation (%) | 5.2 | 8.3 | 5.6 |

[Fig. 7]
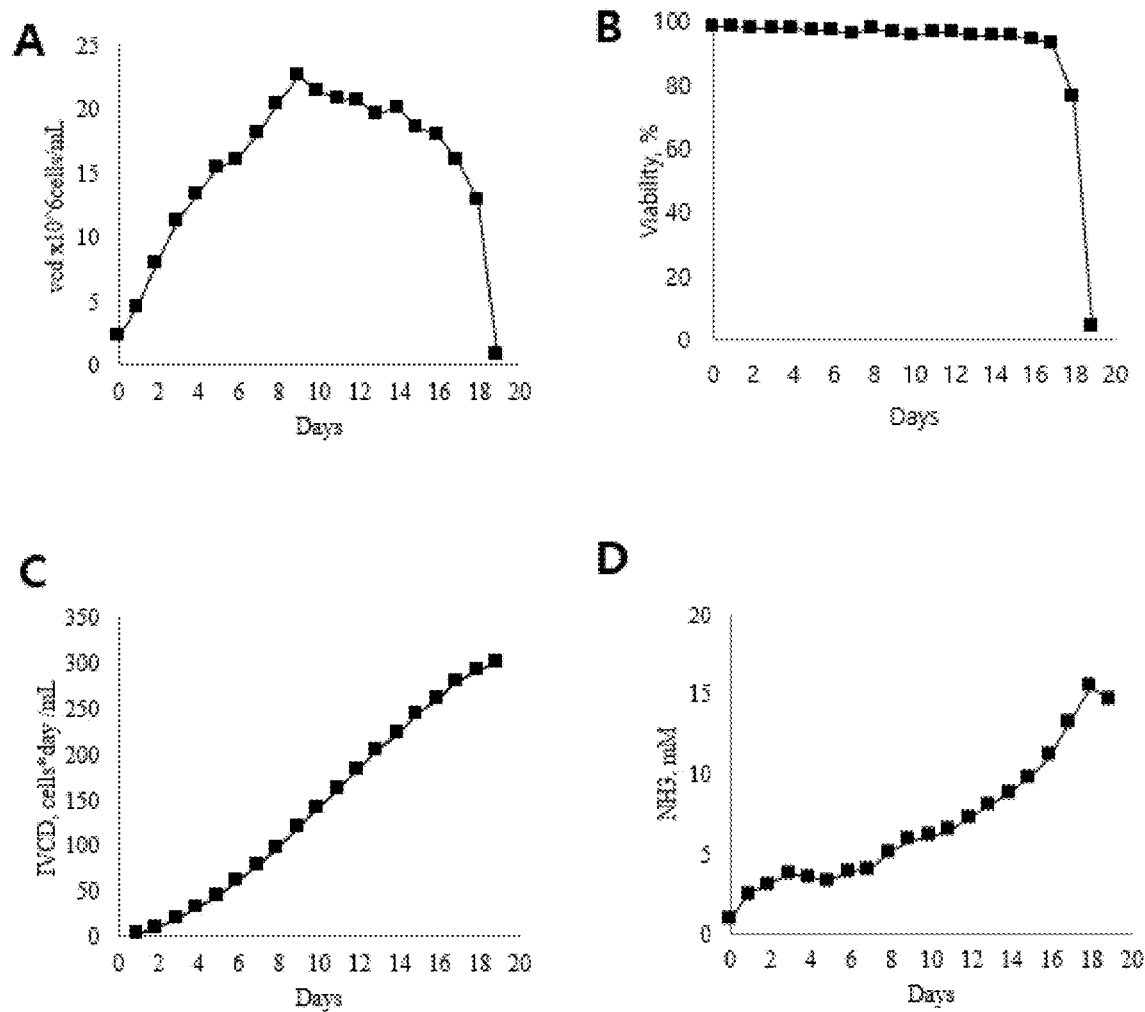

[Fig. 8]
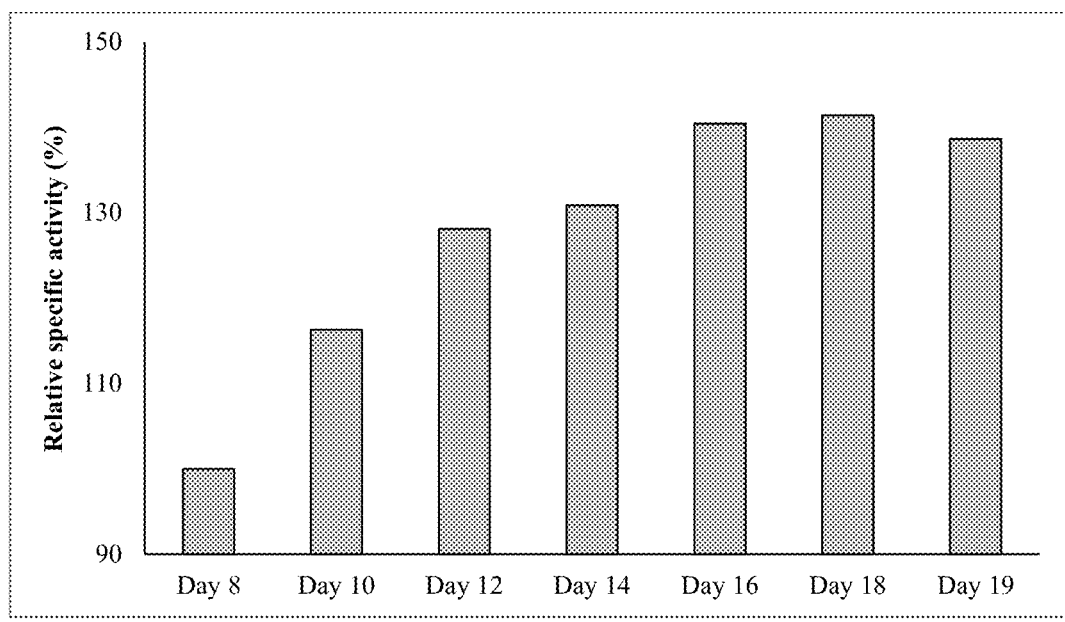

[Fig. 9]
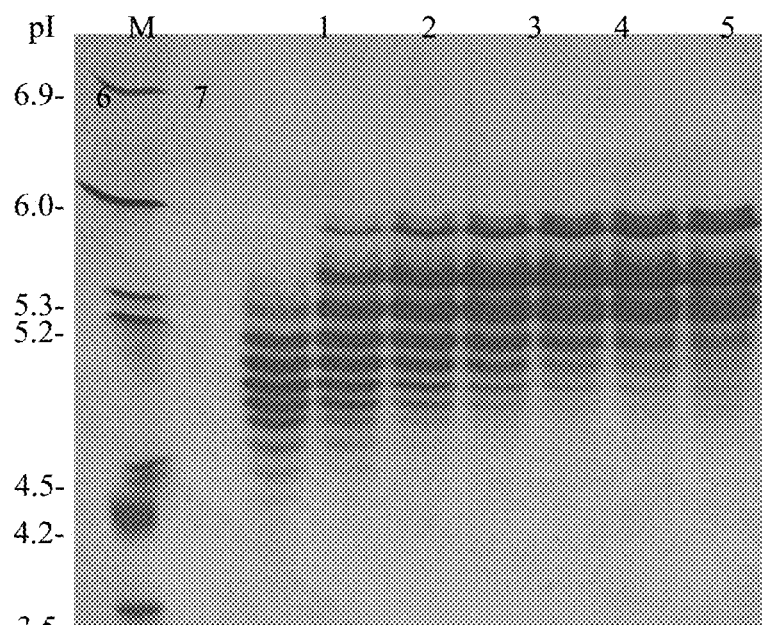
Coomassie G / IEF pH3-7

[Fig. 10]
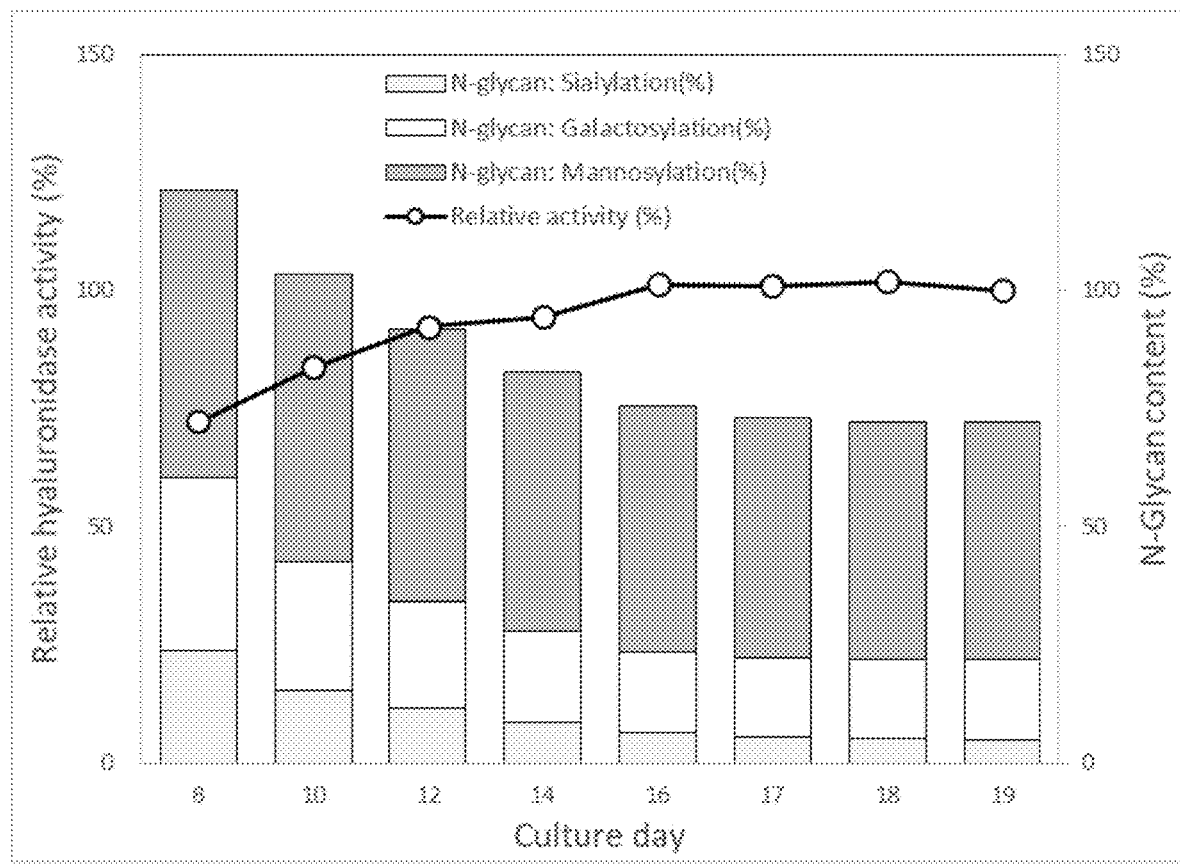

[Fig. 11]
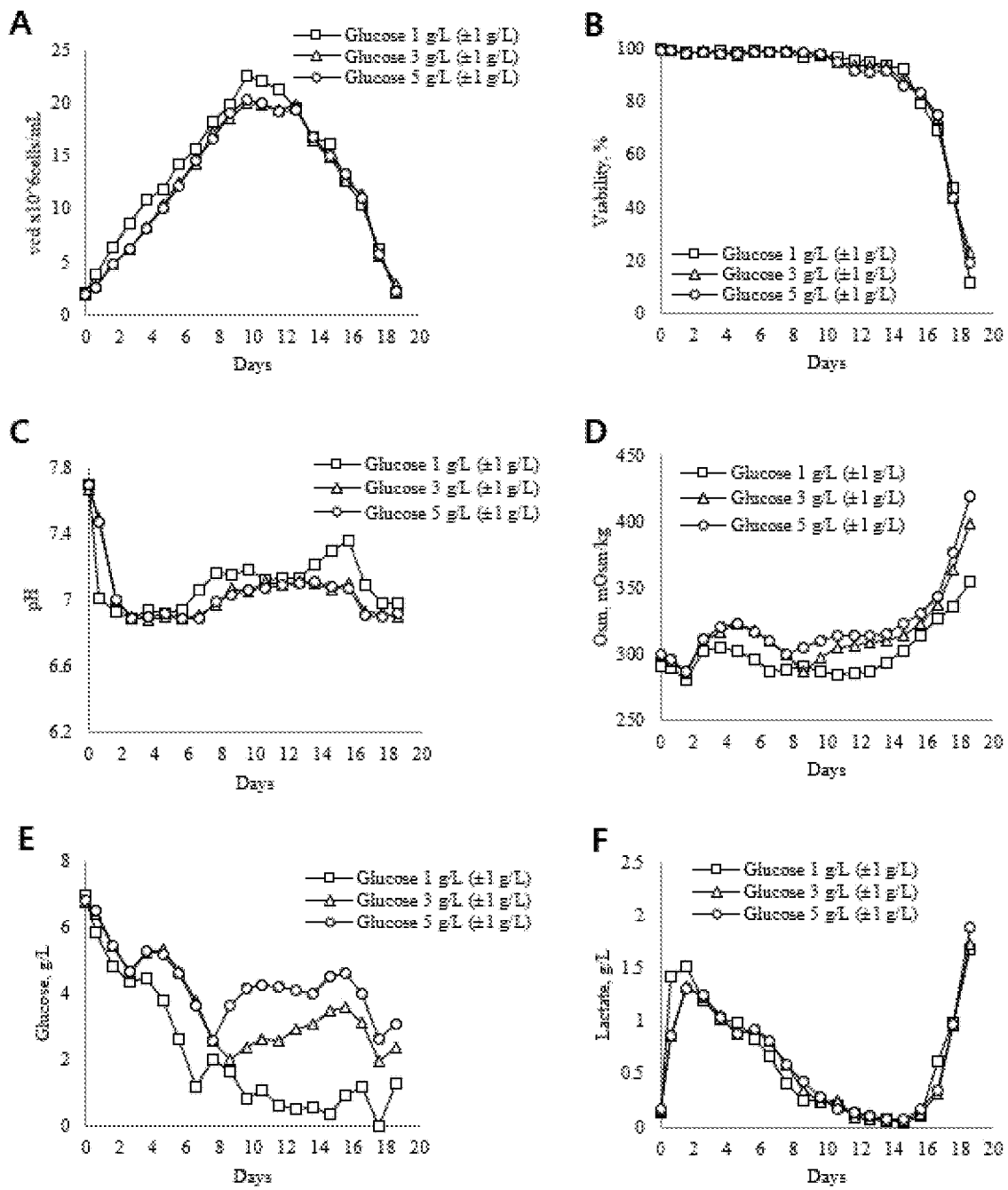

[Fig. 12]
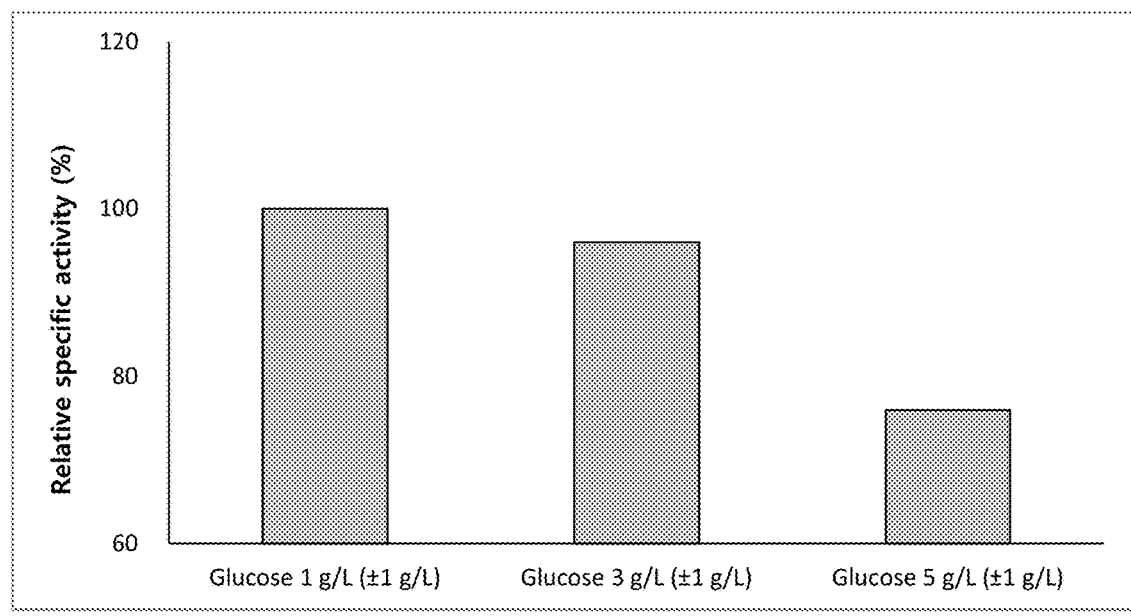

[Fig. 13]
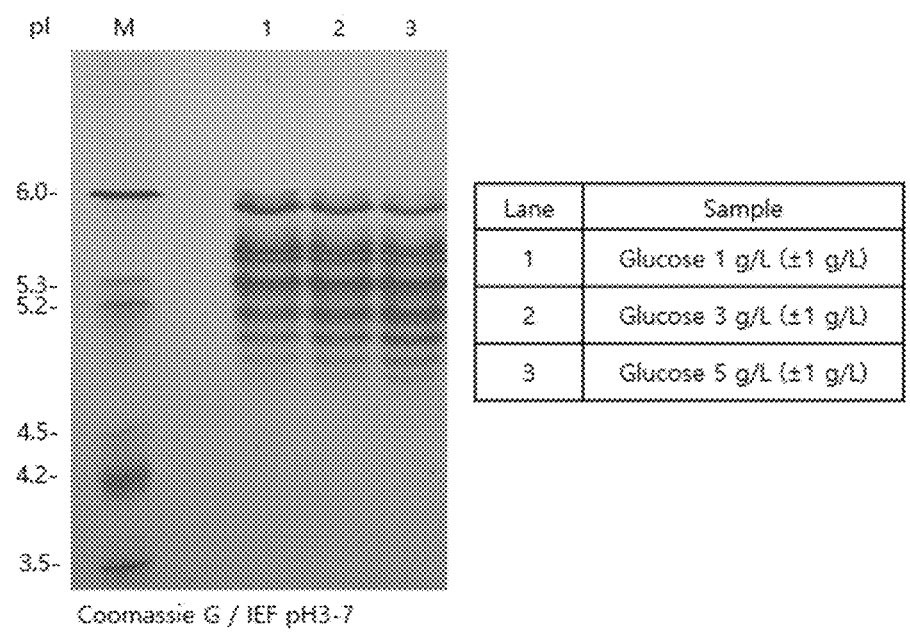

[Fig. 14]

| N-Glycan pattern | Residual Glucose 1 g/L (±1 g/L) | Residual Glucose 3 g/L (±1 g/L) | Residual Glucose 5 g/L (±1 g/L) |
|---|---|---|---|
| Galactosylation (%) | 39.4 | 41.2 | 52.2 |
| Sialylation (%) | 12.7 | 14.4 | 21.4 |
| Mannosylation (%) | 49.7 | 49.3 | 46.1 |
| Total afucosylation (%) | 53.6 | 52.6 | 50.7 |
| Afucosylation (%) | 7.5 | 7.6 | 9.2 |

[Fig. 15]
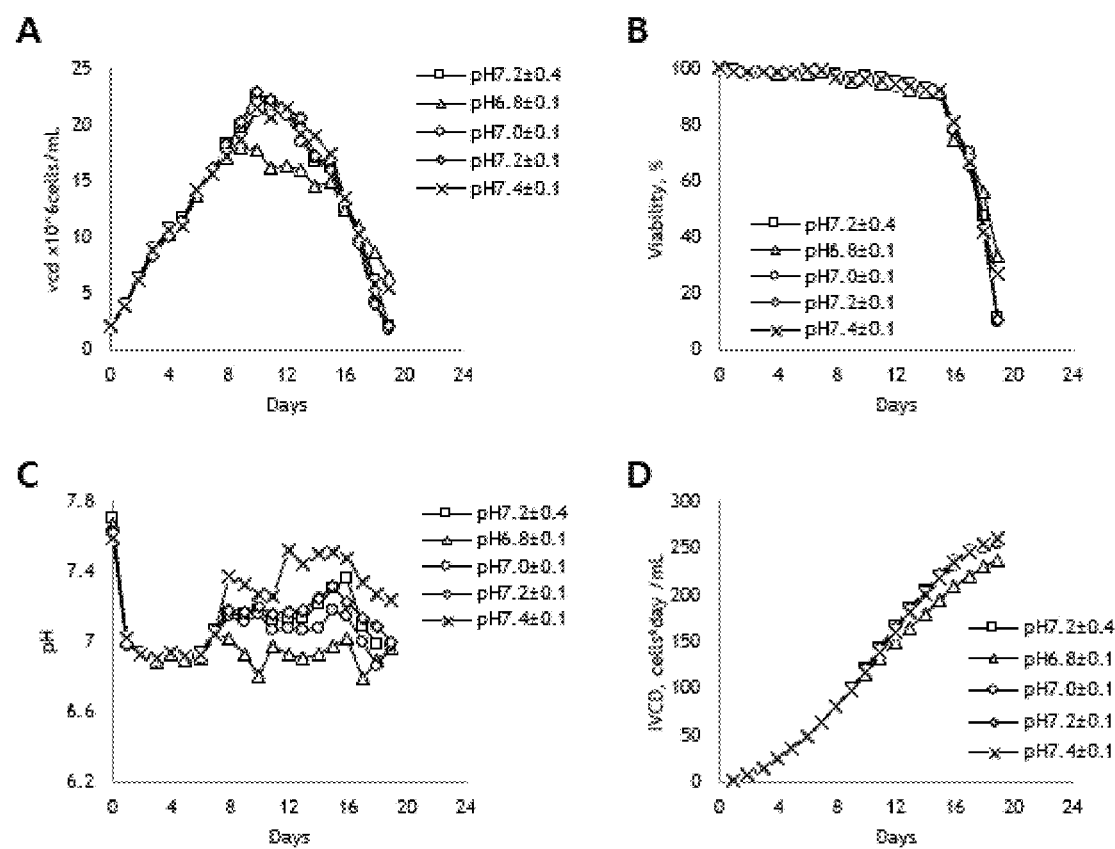

[Fig. 16]
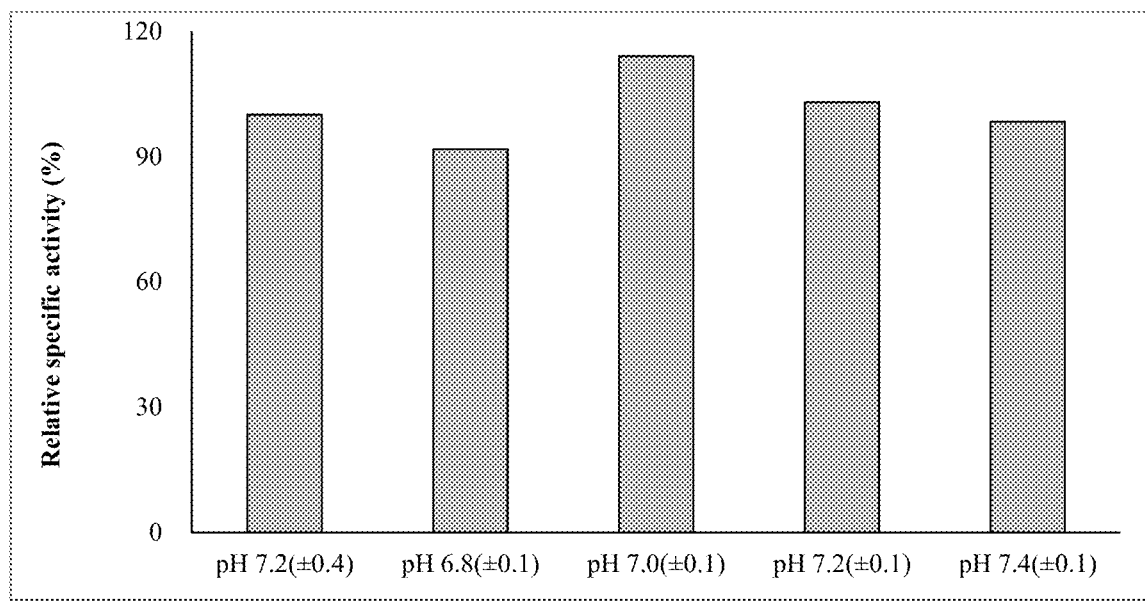

[Fig. 17]
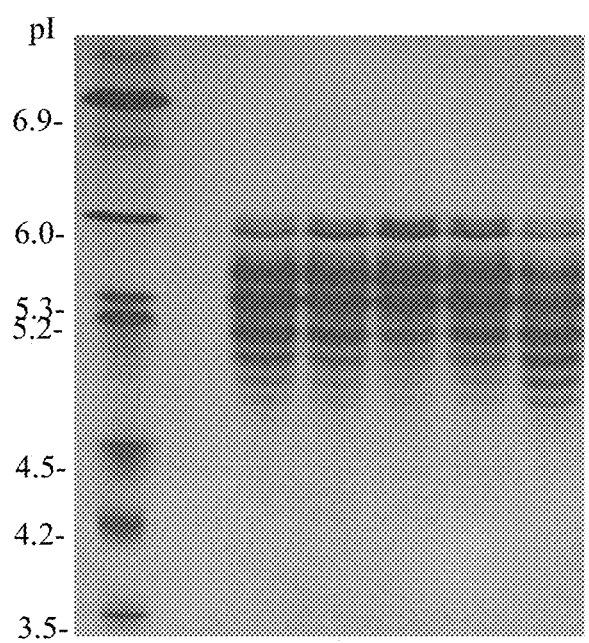

[Fig. 18]
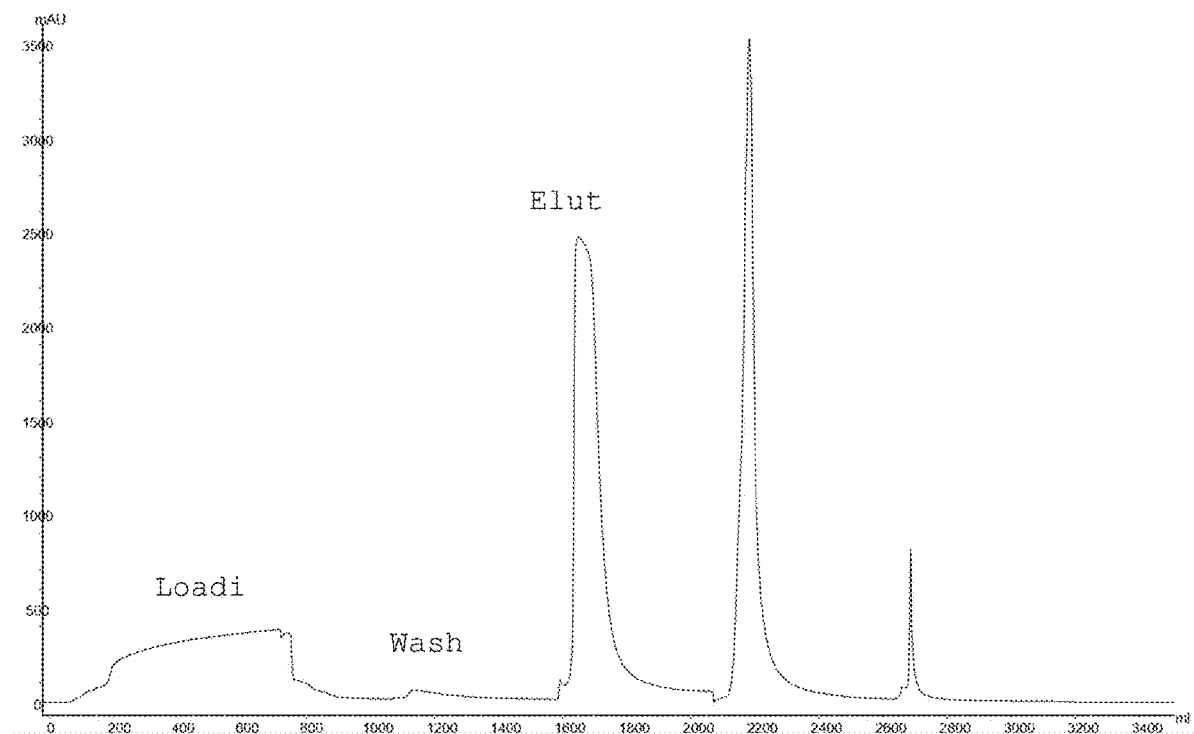

[Fig. 19]
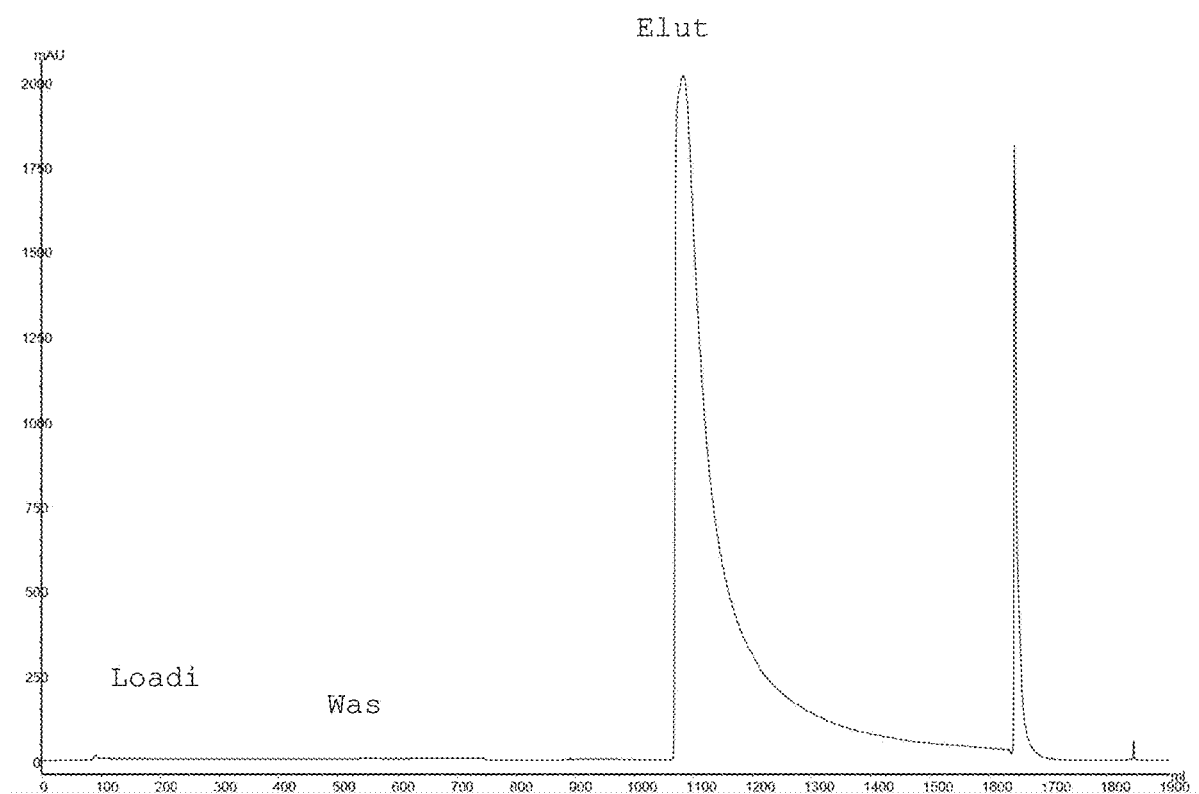

[Fig. 20]
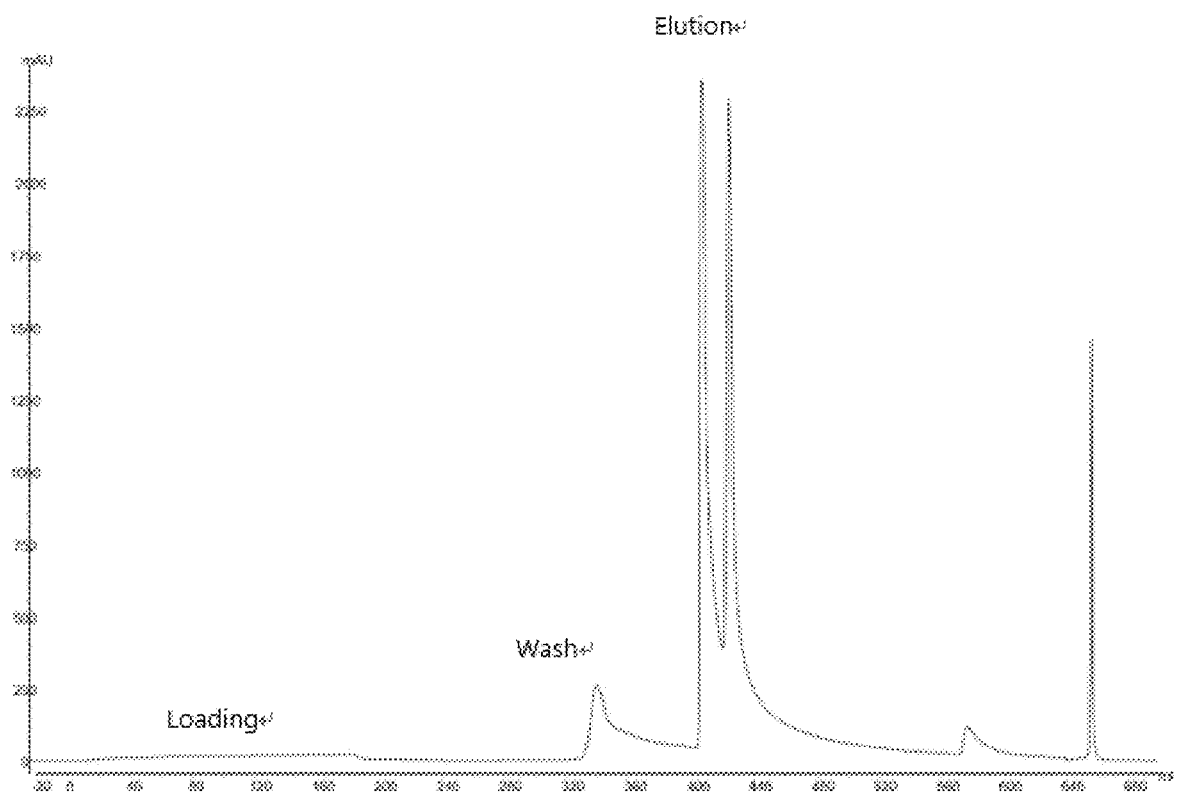

METHOD FOR PRODUCING RECOMBINANT HYALURONIDASE

CROSS-REFERENCE TO RELATED APPLICATIONS

This is a U.S. national phase under the provisions of 35 U.S.C. § 371 of International Patent Application No. PCT/KR2021/010368 filed Aug. 6, 2021, which in turn claims the priority under 35 U.S.C. § 119 of Korean Patent Application No. 10-2020-0099100 filed Aug. 7, 2020. The disclosures of all such applications are hereby incorporated herein by reference in their respective entireties, for all purposes.

REFERENCE TO SEQUENCE LISTING

This application includes an electronically submitted sequence listing in .txt format. The .txt file contains a sequence listing entitled "651_SeqListing_ST25.txt" created on Sep. 27, 2022 and is 8,075 bytes in size. The sequence listing contained in this .txt file is part of the specification and is hereby incorporated by reference herein in its entirety.

BACKGROUND OF THE INVENTION

Field of the Invention

The present invention relates to a method for producing hyaluronidase PH20 variants which include one or more amino acid residue substitutions, and optionally include deletions of some N-terminal and/or C-terminal amino acid residues in hyaluronidase, in particular, wild-type or mature wild-type PH20, or wild-type or mature wild-type PH20 amino acid sequences.

Description of the Related Art

Hyaluronidases are enzymes that degrade hyaluronic acid present in the extracellular matrix. Hyaluronidases hydrolyze hyaluronic acid to thereby reduce the viscosity of hyaluronic acid in the extracellular matrix and increase the permeability into tissues (skin) (Bookbinder et al., 2006). Hyaluronidases have been used to enhance absorption of body fluids provided by subcutaneous injection [Muchmore et al., 2012] or intramuscular injection [Krantz et al., 2016] and to improve the diffusion of local anesthetics [Clement et al. al., 2003]. Drugs that promote subcutaneous administration in this way include morphine [Thomas et al., 2009], Ceftriaxone [Harb et al., 2010], insulin [Muchmore et al., 2012], and immunoglobulin [Wasserman et al., 2014]. Hyaluronidases are also used to improve the dispersion of fluids or drugs leaked into tissues by intravenous injection or hematoma diffusion. Among hyaluronidases, a recombinant human PH20 protein having activity at neutral pH was developed by Halozyme Therapeutics Inc., and is sold under the trade name "Hylenex" (Bookbinder et al., 2006).

Recombinant human PH20 proteins have been reported to be expressed in yeast (P. pastoris), DS-2 insect cells, and animal cells. The recombinant PH20 proteins produced in insect cells and yeast differ from human PH20 in terms of the pattern of N-glycosylation during post-translational modification, thus affecting the activity thereof and entailing the risk of side effects occurring in the body.

For biopharmaceutical development, product consistency and long shelf life are important factors which provide manufacturing flexibility. During manufacture, various types of microheterogeneities occur due to differences in size and charge resulting from enzymatic or spontaneous degradation and modifications. Each of chemical and enzymatic modifications such as deamidation and sialylation increases the net negative charges and decreases the pI value in the antibody, thereby forming acidic variants [Harris R J et al., 2004]. In addition, C-terminal lysine cleavage results in loss of net positive charges and formation of acidic variants. Formation of basic variants may result from C-terminal lysine or glycine amidation, succinimide formation, amino acid oxidation, or sialic acid removal, which removes additional positive or negative charges; both types of modification increase the pI value [Harris R J et al., 2004].

Glycosylation is a post-translational process of proteins in cells (eukaryotes), and occurs in the endoplasmic reticulum and the Golgi apparatus. Glycosylation is classified into N-glycosylation and O-glycosylation, which differ depending on the functional group that is attached. The process of attaching sugars such as lactose or fucose to proteins produced in cells is broadly referred to as "glycosylation". When a glycan is linked to a protein through glycosylation, the protein undergoes a "folding" process to form a three-dimensional structure. This imparts stability to the protein so that it can be maintained for a long time without being released (unfolded). This glycan is a crucial process which serves to enable communication and information exchange between cells.

There are two types of reactions for adding glycans to proteins: N-linked or O-linked glycosylation. These two glycosylation processes differ in the glycan synthesis and addition mechanism, and among them, the mechanism and role of N-glycosylation are better known. Glycans added through N-glycosylation are called "N-glycans" and are formed in the endoplasmic reticulum. A series of ALG (asparagine-linked glycosylation) enzymes on dolichol pyrophosphate (PP-Dol) present in the endoplasmic reticulum membrane are added with N-acetylglucosamine (GlcNAc), mannose (Man), glucose (Glc), etc. to finally synthesize Glc3Man9GlcNAc2-PP-Dol, which is a complex glycan in the form of a lipid-linked oligosaccharide (LLO). The synthesized LLO is transferred to the N-glycosylation sequence of a peptide including N-x-S/T, which is directly translated from the ribosome to the endoplasmic reticulum through a co-translational translocation mechanism by an oligosaccharyltransferase composed of 8 or more subunits. The N-glycans attached to the proteins are removed one by one from the terminal of the glycan by glucosidase (α-Glucosidase I, Gls1p; aglucosidase II, Glsp II) present in the endoplasmic reticulum. Because the second and third glucoses are removed more slowly, folding is completed with the help of the lectin chaperones, calnexin and calreticulin. When all glucose is cleaved out, protein folding is recognized as complete, and Man8GlcNAc2 glycans attached thereto are transferred to the Golgi apparatus. In this regard, there is a quality control process of once again verifying the folding of glycoproteins before transferring the same from the ER to the Golgi. When proper folding is not achieved, the process of giving a chance to complete folding by allowing one molecule of glucose to enter the calnexin/calreticulin cycle is repeated.

The initial process of biosynthesis of N-glycans in the endoplasmic reticulum described above is conserved in almost the same manner across a wide range of organisms from yeast, a simple eukaryotic microorganism, to animals, that is, higher organisms. However, the glycans transferred to the Golgi apparatus undergo various glycan modifications specific to each species, resulting in the formation of completely different types of glycans in yeast, insects, plants, and animals. However, these various glycans also share a core site in common, namely the structure in which three mannose and two GlcNAc are linked to the nitrogen of asparagine, which is called a "trimannosyl core". The form in which mannose is mainly connected to the trimannosyl core is called a "high-mannose type", and is often found in yeast and mold. A structure in which dozens of mannose are consecutively added to the Golgi apparatus is also found in *Saccharomyces cerevisiae*, which is a well-known yeast. On the other hand, glycoproteins having glycans of the deficient mannose type (Pauci-mannose type) are found in insect cells. These are first trimmed to form Man5GlcNAc2 by mannosidase IA, IB & IC in the Golgi apparatus, N-acetyl-glucosaminyltransferase (GNT) I acts to add one GlcNAc to the Man5GlcNAc2, and then mannosidase II acts to form a hybrid structure in which one GlcNAc is added to the trimannosyl core. Then, the added GlcNAc is cleaved off again, forming a deficient mannose-type glycan structure. In animal cells, α(1,6)-fucose is often added to the first GlcNAc bound to an asparagine residue. In animals, GNT II acts on the structure in which one GlcNAc is added to the trimannosyl core and another GlcNAc is added thereto, forming a glycan having two antenna structures. Then, GNT IV and V may act to form four-antenna structures, and in some cases, GNT VI, IX, or VB may act to form six-antenna structures. After GlcNAc is added to form the antenna skeleton, β-galactosyltransferase and α-sialyltransferase present in the Golgi body act to form a complex glycan structure in which galactose and sialic acid are added to GlcNAc.

N-glycosylation may greatly affect the folding or activity of proteins, and there is a very high possibility that the presence of glycosylation and the structure or form of glycans may vary depending on the host cell type, recombinant manipulation method, and culture conditions (Schilling, et al., 2002) when producing proteins or variants thereof present in nature using genetic engineering methods for industrial application. That is, quantitative differences in the structure of the glycan or the sugar components constituting the glycan occur depending on the differences in production conditions during the protein production process. Culture conditions affecting N-glycosylation include glucose or glutamine concentration in the culture medium (Tachibana et al. 1994), concentration of dissolved oxygen (DO) (Restelli et al. 2006), culture medium pH (Borys et al. 1993), concentration of ammonia of culture medium (Borys et al. 1994), culture temperature (Clark et al. 2004), and the like.

In general, an enzyme specifically binds to a substrate to form an enzyme-substrate complex, which acts as a catalyst to lower the activation energy of the reaction and promotes the reaction of the enzyme. An enzyme can discriminate between a substrate and molecules that compete with the substrate, and is capable of specifically binding to the substrate due to the distribution of complementary charges at the position at which the enzyme binds to the substrate, a complementary structure, and distribution of hydrophilicity and hydrophobicity. A lock-and-key model in which the enzyme and the substrate are complementary to each other and have geometric shapes has been proposed in order to elucidate the binding position of the enzyme, but does not satisfactorily explain the transition state of the enzyme-substrate complex. According to an induced-fit model suggested to overcome this problem, as the enzyme and substrate continue to interact with each other in the enzyme-substrate complex, they change the structure thereof based on the flexible structure of the enzyme protein. In this process, the reaction can be further facilitated by the distribution of surrounding electric charges by amino acid residues or N-glycans constituting the active sites, or by the distribution of hydrophilicity/hydrophobicity.

Moreover, charge interaction is essential for the reaction of a hyaluronidase, which is an enzyme that hydrolyzes hyaluronic acid as a substrate. Arming et al. revealed that an arginine residue having positive charges in hyaluronidase PH20 is essential for enzymatic activity for binding to hyaluronic acid, which is a substrate having a large amount of negative charges distributed therein (Arming et al. 1997). Therefore, it can be inferred that the charge distribution of the N-glycan also affects such enzymatic activity. It is important to prove that when hyaluronic acid, which is a substrate having a large amount of negative charges, binds to a hyaluronidase, the level of negatively charged sialic-acid-capping sugars in the N-glycans, that is, the sialylation level, affects the formation of the enzyme-substrate complex or the progress of the enzymatic reaction. In order to limit the sialylation level, the transfer of sialic acid to the galactose residue should be limited, desialylation should be performed, or the galactosylation level should be limited.

Therefore, the productivity and activity of recombinant hyaluronidase PH20 and variants thereof are affected by changes in the level of N-glycans, so research to develop a method of producing hyaluronidase PH20 or a variant thereof that is highly active and productive and is industrially useful by controlling and maintaining the level of N-glycans is required for efficient mass-production in the art.

SUMMARY OF THE INVENTION

Therefore, the present invention has been made in view of the above problems, and it is one object of the present invention to provide a method for culturing host cells that produce recombinant hyaluronidase PH20 or a variant thereof, and hyaluronidase PH20 or a variant thereof prepared by this method, in particular, a method for producing hyaluronidase PH20 or a variant thereof having improved enzymatic activity and productivity.

The objects of the present invention are not limited to those described above. Other objects not described herein will be clearly understood to those skilled in the art from the following disclosure.

In the present invention, when the host cells for producing recombinant hyaluronidase PH20 or a variant thereof are cultured under specific culture conditions, the N-glycosylation characteristics of the produced recombinant hyaluronidase PH20 or a variant thereof, and furthermore, the enzymatic activity of the produced hyaluronidase PH20 or a variant thereof, are remarkably improved.

Specifically, it was found that it is effective to increase the activity of the produced hyaluronidase PH20 or a variant thereof by controlling the sialylation, galactosylation and/or mannosylation levels, in particular, the sialylation level in the N-glycans, and that the enzymatic activity and productivity of the hyaluronidase PH20 or a variant thereof according to the present invention can be remarkably improved by performing culture for a certain time period after changing the culture temperature.

Specifically, the method for producing hyaluronidase PH20 or a variant thereof according to the present invention comprises:

(1) culturing host cells expressing recombinant hyaluronidase PH20 or a variant thereof at a culture temperature of 35° C. to 38° C. to an integral viable cell
(2) of $20\times10^6$ to $120\times10^6$ cells×day/mL; and
(2) decreasing the culture temperature to 28° C. to 34° C. and then culturing the host cells for 2 to 18 days while maintaining the culture temperature in accordance with at least one method selected from the group consisting of:
(a) culturing the host cells while maintaining the concentration of the residual glucose in a medium between 0.001 g/L and 4.5 g/L for the culture period; and
(b) culturing the host cells while maintaining a pH of the culture medium at 6.8 to 7.2.

The PH20 or a variant thereof produced by the production method according to the present invention is characterized in that the sialylation content of the N-glycan of the produced PH20 or variant thereof is 1 to 38%, whereby the enzymatic activity is remarkably increased, but is not limited thereto, and the value is an experimental value having an error range of 10%. The reason for this is that deviations occur depending on conditions such as the equipment used for culture and the work proficiency of the tester when setting culture conditions, so the numerical values set in the present invention should be interpreted in a broader sense in consideration of deviations rather than in a narrow sense. The host cells may be cultured by one or more methods selected from the group consisting of batch culture, repeated batch culture, fed-batch culture, repeated fed-batch culture, continuous culture, and perfusion culture.

BRIEF DESCRIPTION OF THE DRAWINGS

The above and other objects, features and other advantages of the present invention will be more clearly understood from the following detailed description taken in conjunction with the accompanying drawings, in which:

FIG. 1 illustrates the result of analysis of enzymatic activity, isoelectric focusing pattern, and N-glycan content with respect to wild human hyaluronidase PH20 and variants thereof, wherein
A illustrates the enzymatic activity of wild human hyaluronidase PH20 and variants thereof,
B illustrates the result of isoelectric focusing of each sample, and
C illustrates the N-glycan content;

FIG. 2 illustrates the result of comparative analysis in the enzymatic activity and isoelectric focusing pattern between purified hyaluronidase PH20 variant fractions treated with PNGase F, sialidase A, and sialidase A+galactosidase, wherein
A illustrates the result of isoelectric focusing of each sample,
B illustrates the enzymatic activity, and
C illustrates the N-glycan content;

FIG. 3 illustrates the result of analysis of changes in cell growth, cell viability, pH, and lactate concentration depending on culture conditions of addition of N-acetyl-D-mannosamine or galactose with respect to cells producing hyaluronidase PH20 variants, wherein
A illustrates the change in cell growth,
B illustrates the change in cell viability,
C illustrates the change in pH, and
D illustrates the change in lactate concentration;

FIG. 4 is a graph showing the activity of the harvested cell culture fluid for producing hyaluronidase PH20 variants depending on culture conditions of addition of N-acetyl-D-mannosamine or galactose;

FIG. 5 illustrates the result of isoelectric focusing analysis of the harvested cell culture fluid for producing hyaluronidase PH20 variants depending on culture conditions of addition of N-acetyl-D-mannosamine or galactose;

FIG. 6 illustrates the result of N-glycan structure analysis of the harvested cell culture fluid for producing hyaluronidase PH20 variants depending on culture conditions of addition of N-acetyl-D-mannosamine or galactose;

FIG. 7 illustrates the changes in cell growth, cell viability and ammonia concentration of cells for producing hyaluronidase PH20 variants as a function of number of days of culture, wherein
A illustrates the change in cell growth,
B illustrates the change in cell viability,
C illustrates the change in integral viable cell density, and
D illustrates the change in ammonia concentration;

FIG. 8 is a graph showing the specific activity of the harvested cell culture fluid for producing hyaluronidase PH20 variants as a day of cell culture;

FIG. 9 illustrates the result of isoelectric focusing of the harvested cell culture fluid for producing hyaluronidase PH20 variants as a day of cell culture;

FIG. 10 illustrates the results of N-glycan structure and activity analysis of the harvested cell culture fluid for producing hyaluronidase PH20 variants as a day of cell culture;

FIG. 11 illustrates changes in cell growth depending on glucose concentration conditions, cell viability, pH, osmolality, glucose concentration, and lactate concentration with respect to cells for producing hyaluronidase PH20 variants, wherein
A illustrates the change in cell growth,
B illustrates the change in cell viability,
C illustrates the change in pH,
D illustrates the change in osmolality,
E illustrates the change in glucose concentration, and
F illustrates the change in lactate concentration;

FIG. 12 is a graph showing the specific activity of the harvested cell culture fluid for producing hyaluronidase PH20 variants depending on the glucose concentration;

FIG. 13 illustrates the result of isoelectric focusing of the harvested cell culture fluid for producing hyaluronidase PH20 variants depending on the glucose concentration;

FIG. 14 illustrates the result of N-glycan structure analysis of the harvested cell culture fluid for producing hyaluronidase PH20 variants depending on the glucose concentration;

FIG. 15 illustrates the result of analysis of changes in cell growth, cell viability, pH, and lactate integral of Viable Cell Density depending on pH levels with respect to cells producing hyaluronidase PH20 variants, wherein
A illustrates the change in cell growth,
B illustrates the change in cell viability,
C illustrates the change in pH, and
D illustrates the change in integral viable cell density;

FIG. 16 is a graph showing the specific activity of the harvested cell culture fluid of the cells for producing hyaluronidase PH20 variants depending on PH levels;

FIG. 17 illustrates the result of isoelectric focusing of the harvested cell culture fluid for producing hyaluronidase PH20 variants depending on pH levels;

FIG. 18 is a purification chromatogram obtained through primary anion exchange resin chromatography during purification of the hyaluronidase PH20 variant;

FIG. 19 is a purification chromatogram obtained through secondary anion exchange resin chromatography during purification of the hyaluronidase PH20 variant; and FIG. 20 is a purification chromatogram obtained through cation exchange resin chromatography during purification of the hyaluronidase PH20 variant.

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

The present invention is based on the finding that the sialylation, galactosylation and/or mannosylation levels, in particular, the sialylation level of the N-glycan, are crucial for the enzymatic activity and productivity of hyaluronidase PH20 or variants thereof when producing the hyaluronidase PH20 or variants thereof for industrial application using a genetic engineering method.

Specifically, it was found that when the sialylation content of the N-glycan of PH20 or the variant thereof is 1 to 38%, preferably 1 to 30%, more preferably 1.5 to 28%, and most preferably 2 to 25%, the enzymatic activity and productivity of hyaluronidase PH20 or a variant thereof were improved to unexpectedly high levels.

More specifically, it was found that when the galactosylation level of the N-glycan of PH20 or a variant thereof is 1 to 68%, the sialylation content thereof is 1 to 38%, and the mannosylation content thereof is 40 to 63%, preferably, when the galactosylation content thereof is 5 to 60%, the sialylation thereof is 1 to 30%, and the mannosylation content thereof is 42 to 62%, more preferably, when the galactosylation content thereof is 10 to 56%, the sialylation content thereof is 1.5 to 28%, the mannosylation content thereof is 44 to 61%, and most preferably when the galactosylation content thereof is 15 to 50%, the sialylation content thereof is 2 to 25%, and the mannosylation content thereof is 47 to 60%, the enzymatic activity and productivity of hyaluronidase PH20 or a variant thereof were improved to unexpectedly high levels.

The above numerical values are derived from the experimental results of Examples shown in Table 1, and are numerical values obtained with a 95% confidence interval, and such numerical values may also include an error of 10%. This is because there is variation in measurement of the sugar (glucose) levels in proteins, depending on conditions such as the equipment used for the experiment, the enzymatic reaction time, the test temperature, the proficiency of the tester, and the like, so the glucose level measured in the present invention should be interpreted in a broader sense in consideration of variation between laboratories, rather than in a limited sense.

In the present invention, the galactosylation proportion (%) of the N-glycans is the sum of the proportion (%) of glycans containing galactose at the terminal thereof, such as G1, G1F, G1F', G2, G2F, A1, A1F, A2, and A2F, among the N-glycans, the sialylation proportion (%) is the sum of the proportion (%) of N-glycans containing sialic acid at the terminal thereof, such as A1, A1F, A2, and A2F, among the N-glycans, and the mannosylation proportion (%) is the sum of N-glycans containing mannose at the terminal thereof, such as M4G0F, M5, M5G0, M6, M7, and M8, among the N-glycans.

Specifically, the method for producing hyaluronidase PH20 or a variant thereof having a sialylation content in the N-glycan of 1 to 38% according to the present invention includes:

(1) culturing host cells expressing recombinant hyaluronidase PH20 or a variant thereof at a culture temperature of 35° C. to 38° C. to an integral viable cell density of $20\times10^6$ to $120\times10^6$ cells×day/mL; and (2) decreasing a culture temperature to 28° C. to 34° C. and then culturing the host cells for 2 to 18 days while maintaining the culture temperature in accordance with at least one method selected from the group consisting of:

(a) culturing the host cells while maintaining the concentration of the residual glucose in the medium between 0.001 g/L and 4.5 g/L for a culture time period; and (b) culturing the host cells while maintaining a pH of the culture medium at 6.8 to 7.2.

The above value is an experimental value having an error range of 10%. The reason for this is that variation occurs depending on conditions such as the equipment used for culture and the work proficiency of the tester when setting culture conditions, so the numerical values set in the present invention should be interpreted in a broader sense in consideration of such variation rather than in a narrow sense.

The decrease of the culture temperature from step (1) to step (2) is performed when an integral viable cell density reaches $20\times10^6$ to $120\times10^6$ cells×day/mL, preferably $40\times10^6$ to $100\times10^6$ cells×day/mL, more preferably, $60\times10^6$ to $80\times10^6$ cells×day/mL, but is not limited thereto.

In addition, the culture time period in step (2) may be 2 to 18 days, preferably 3 to 16 days, more preferably 4 to 14 days, but is not limited thereto.

For example, in the case of using a fed-batch culture method in the production of PH20 or a variant thereof according to the present invention, the productivity of PH20 or a variant thereof can be maximized and the enzymatic activity of the produced PH20 or a variant thereof can be remarkably improved by performing seed culture immediately before main culture at 35° C. to 38° C. through perfusion culture or fed-batch culture until a cell concentration reaches a certain level and then performing main culture through inoculation at a decreased temperature lower than 35° C. for 2 to 18 days, preferably 3 to 16 days, more preferably 4 to 14 days.

The cell inoculation concentration of the main culture may be $1\times10^5$ cells/mL or more, preferably $5\times10^5$ cells/mL or more, and more preferably $1\times10^6$ cells/mL or more, but is not limited thereto.

By performing culture using a combination of fed-batch culture and perfusion culture in the production of PH20 or a variant thereof according to the present invention, the productivity of PH20 or a variant thereof can be maximized and the enzymatic activity of the produced PH20 or a variant thereof can be markedly increased.

In the present invention, the residual glucose concentration in the medium during culture is maintained at 0.001 g/L to 4.5 g/L, preferably 0.01 to 4.0 g/L, and more preferably 0.1 to 3.5 g/L, but the present invention is not limited thereto.

As used herein, the expression "residual glucose concentration in the medium during culture is maintained at 0.001 g/L to 4.5 g/L, preferably 0.01 to 4.0 g/L, and more preferably 0.1 to 3.5 g/L" means that when the residual glucose concentration in the medium, measured during the culture period at intervals of 1 to 36 hours, preferably 3 to 30 hours, more preferably 6 to 24 hours, or in real time, is lower than a set reference concentration of 0.001 g/L to 4.5 g/L, preferably 0.01 to 4.0 g/L, and more preferably 0.1 to 3.5 g/L, a glucose stock solution is added to the medium to obtain the corresponding reference concentration upon culture.

In the present invention, it will be apparent to those skilled in the art that the reference concentration of the residual glucose concentration in the medium may be set within 0.001 g/L to 4.5 g/L, preferably 0.01 to 4.0 g/L, and more preferably 0.1 to 3.5 g/L, and the reference concentration may be appropriately changed during the culture period. For example, the reference concentration of residual glucose in the medium is 2 g/L on the 1st and 2nd days of culture, the reference concentration is lowered to 1.5 g/L on the 3rd to 5th days of culture, and the reference concentration is increased to 2 g/L, or is set to a level lower than 1.5 g/L, such as 1.0 g/L, thereafter.

The hyaluronidase PH20 or a variant thereof, which is produced by the method according to the present invention and has predetermined sialylation, galactosylation, and/or mannosylation levels in the N-glycan portion, has activity in a culture medium of the hyaluronidase enzyme, of 10,000 units/mL, preferably 11,000 units/mL or more, more preferably 12,000 units/mL or more, but is not limited thereto.

In addition, the hyaluronidase PH20 or a variant thereof, which is produced by the method according to the present invention and has predetermined sialylation, galactosylation and/or mannosylation contents in the N-glycan, is a wild human PH20 produced by a conventional method and has enzymatic activity increased by 10% or more, preferably 12% or more, more preferably 15% or more, than the activity of wild human PH20 produced by a conventional method, but the present invention is not limited thereto.

Preferably, in the method for producing hyaluronidase PH20 or a variant thereof according to the present invention, culture of the host cells in step (1) and/or step (2) may be performed under one or more conditions selected from the group consisting of: (i) adding ammonia to a medium or increasing an ammonia concentration in the medium to 5 mM or more; (ii) adding one or more substances selected from the group consisting of glutamine, glucosamine, uridine, glucosamine, and sodium butyrate to the medium; and (iii) not adding galactose and manNAc to the medium, but the method is not limited thereto.

More specifically, in the method for producing hyaluronidase PH20 or a variant thereof according to the present invention, the culture of host cells in step (1) and/or step (2) may be performed by adding ammonia to the medium, increasing the ammonia concentration to 5 mM or more, adding glutamine thereto, not adding galactose and manNAc thereto, adding uridine or glucosamine thereto, and adding sodium butyrate thereto, but the method is not limited thereto.

As used herein, the term "hyaluronidase PH20 or a variant thereof" refers to an enzyme that degrades hyaluronic acid disposed in an extracellular matrix.

The term "hyaluronidase PH20" or "PH20" as used herein is interpreted to include both wild PH20 and a mature form thereof, and the term "variant of hyaluronidase PH20 or PH20" means a PH20 variant which includes substitutions, deletions and insertions of one or more amino acid residues and optionally includes deletions of some of the N-terminal and/or C-terminal amino acid residues in the amino acid sequence of "hyaluronidase PH20" or "PH20", but is not limited thereto.

The hyaluronidase according to the present invention refers to a hyaluronidase which is derived from an animal or a microorganism such as Streptomyces, and has hyaluronidase activity, among which "hyaluronidase PH20" or "PH20" is derived from an animal or microorganism such as Streptomyces, and is preferably derived from humans, cattle, or sheep.

Human-derived "hyaluronidase PH20" or "PH20 variant" according to the present invention is exemplified in International Patent Publication No. 2020/022791 and U.S. Pat. No. 9,447,401, but is not limited thereto, and is interpreted to include any hyaluronidase or a variant which includes substitutions, deletions and insertions of one or more amino acid residues, optionally includes truncations of one or more amino acid residues of the N-terminal and/or C-terminal amino acid residues in the amino acid sequence of "hyaluronidase PH20" or "PH20", and has hyaluronidase enzymatic activity.

Examples of the host cells used herein for expression of the hyaluronidase proteins may include animal, yeast, actinomycetes and insect cells, and the like, but are not limited thereto.

The animal cells are preferably mammalian cells, more preferably, generally used animal culture cells, such as CHO cells, HEK cells, COS cells, 3T3 cells, myeloma cells, BHK cells, HeLa cells, and Vero cells, and particularly preferably CHO cells for mass expression. In addition, in order to produce desired proteins, in particular, cells suitable for introduction of desired genes, such as dhfr-CHO cells (Proc. Natl. Acad. Sci. USA (1980) 77, 4216-4220) or CHO K-1 cells, which are DHFR gene-knocked out CHO cells (Proc. Natl. Acad. Sci. USA (1968) 60, 1275), or CHO K-1 cells (Proc. Natl. Acad. Sci. USA (1968) 60, 1275) are preferably used. The CHO cells are particularly preferably DG44, DXB-11, K-1 or CHO-S cell lines, and introduction of the vectors into host cells is carried out using a method such as a calcium phosphate method, a DEAE dextran method, electroporation, or a lipoprotein method.

Examples of the yeast include Saccharomyces sp., Hansenula sp., Kluyveromyces, Pichia sp., and the like, and the actinomycetes, for example, includes Streptomyces, but is not limited thereto.

In the method for producing hyaluronidase PH20 or a variant thereof according to the present invention, the culturing of the host cells in step (1) and/or step (2) may be carried out by one or more methods selected from the group consisting of batch culture, repeated batch culture, fed-batch culture, repeated fed-batch culture, continuous culture, and perfusion culture, but is not limited thereto.

Batch culture is a culture method for proliferating cells without adding fresh medium or discharging a culture solution during culture. Continuous culture is a culture method of continuously adding and discharging media during culture. In addition, continuous culture includes perfusion culture. Fed-batch culture falls between batch culture and continuous culture, is also called "semi-batch culture", and involves continuously or sequentially adding media during culture. This culture method prevents discharge of cells even though the culture solution is continuously discharged. In the present invention, any culture method may be used, with fed-batch culture or continuous culture being preferred, and fed-batch culture being particularly preferred.

As described above, in the hyaluronidase PH20 or variant thereof produced by the production method according to the present invention, the specific activity of the enzyme can be increased by 10% or more compared to that produced by a general method, in particular, compared to the specific activity of wild-type human PH20. This increase in enzymatic activity is due to changes in N-glycosylation properties and/or charge modification of the hyaluronidase PH20 or variant thereof produced by the method according to the present invention.

In particular, enzymatic activity increases depending on changes in sialylation, galactosylation, and/or mannosylation, among the patterns of N-glycosylation. These N-glycosylation characteristics, in particular, sialylation, galactosylation and/or mannosylation can be adjusted by the production method according to the present invention.

In the present invention, examples of the covalent bond between glucoses and proteins include an N-glycosidic bond in which N-acetyl-D-glucosamine is covalently linked to an asparagine residue constituting a protein (N-glycoside-linked glycan), an O-glycosidic bond in which N-acetyl-D-galactosamine is covalently bonded to a serine or threonine residue (O-glycoside-linked glycan), and the like, but there is no particular limitation as to the type of covalent bond between glucoses and proteins in the glycoprotein of the present invention, and glycoprotein including one or both of the N-glycoside-linked glycan and the O-glycoside-linked glycan falls within the glycoprotein according to the present invention.

In this aspect, the present invention is directed to a hyaluronidase PH20 or a variant thereof having a sialylation content in an N-glycan content of 1 to 38%, preferably 1 to 30%, more preferably 1.5 to 28%, and most preferably 2 to 25%.

More specifically, the present invention is directed to a hyaluronidase PH20 a variant thereof having a galactosylation content in an N-glycan content of 1 to 68%, a sialylation content in an N-glycan content of 1 to 38%, and a mannosylation content in an N-glycan content of 40 to 63%, preferably a galactosylation content in an N-glycan content of 5 to 60%, a sialylation content in an N-glycan content 1 to 30%, and a mannosylation content in an N-glycan content of 42 to 62%, more preferably a galactosylation content in an N-glycan content of 10 to 56%, a sialylation content in an N-glycan content of 1.5 to 28%, and a mannosylation content in in an N-glycan content of 44 to 61%, and most preferably a galactosylation content in an N-glycan content of 15 to 50%, a sialylation content in an N-glycan content of 2 to 25%, and a mannosylation content in an N-glycan content of 47 to 60%.

The above numerical values are derived from the experimental results of Examples shown in Table 1, and are obtained using a numerical value having a 95% confidence interval, and the numerical values also include an error of 10%. This is because there is variation upon measurement of the glucose contents in proteins depending on conditions such as the equipment used for the experiment, the enzymatic reaction time, the test temperature, the proficiency of the tester, and the like, so the glucose content measured in the present invention should be interpreted in a broader sense in consideration of variation between laboratories, rather than in a limited sense. In addition, charge modification of PH20 or a variant thereof may be identified through isoelectric focusing.

The hyaluronidase PH20 or a variant thereof having specific sialylation and/or galactosylation and mannosylation contents in the N-glycan contents according to the present invention is preferably produced by the production method according to the present invention, but is not limited thereto, but it is obvious that the hyaluronidase PH20 or a variant thereof can be produced by other methods that can be modified by those skilled in the art.

In the present invention, the medium used for culturing cells to express glycoproteins is preferably, but not limited to, a serum-free medium, and DMEM/F12 medium (a combination of DMEM and F12 media) may be used as a basic medium. In addition, commercially available serum-free media, for example, HycellCHO medium, ActiPro medium (HyClone, USA), CD OptiCHO™ medium, CHO-S-SFM II medium or CD CHO medium (Gibco, USA), IS CHO-V™ medium (Irvine Scientific, USA), EX-CELL® Advanced CHO Fed-Batch Medium (Sigma-Aldrich, USA), or the like may be used as a basic medium, but the invention is not limited thereto.

In the present invention, the feed medium used to culture the cells to express glycoproteins is a serum-free medium, and for example, Cell Boost™ 1, Cell Boost™ 2, Cell Boost™ 3, Cell Boost™ 4, Cell Boost™ 5, Cell Boost™ 6, Cell Boost™ 7a/7b (HyClone, USA), CD CHO EfficientFeed™ A AGT™, CD CHO Efficient Feed™ B AGT™, CD CHO EfficientFeed™ C AGT™, CD CHO Efficient Feed™ A plus AGT™, CD CHO EfficientFeed™ B plus AGT™, CD CHO EfficientFeed™ C plus AGT™ (Gibco, USA), BalanCD® CHO Feed 4 (Irvine Scientific, USA), EX-CELL® Advanced CHO Feed (Sigma-Aldrich, USA), CHO-U Feed Mix U1B7/CHO-U Feed Mix U2B13 (Kerry, USA) may be used as a feed medium, but the invention is not limited thereto.

As used herein, the terms "feed medium" and "concentrated nutrient medium" refer to media composed of a specific nutrient or a plurality of nutrients such as amino acids, vitamins, salts, trace elements, lipids, and glucose, and may be concentrated products of the basal medium. The components and concentrations of the produced feed medium may vary depending on the cells to be cultured. In addition, commercially available feed media, for example, Cell Boost Series supplement medium (HyClone, USA), EfficientFeed Supplement medium, GlycanTune feed medium (Gibco, USA), BalanCD CHO feed medium (Irvine Scientific, USA), Cellvento® CHO Cell Culture feed medium (Merck, USA), EX-CELL® Advanced CHO feed medium (Sigma-Aldrich, USA), or the like may be used as the feed medium, but the invention is not limited thereto.

The term "plant-derived hydrolysate" used herein refers to a product extracted from garden peas, cotton seed, wheat gluten, soybeans, or the like and containing no animal-derived components, is a supplement containing large amounts of amino acids, peptides, vitamins, carbohydrates, nucleotides, minerals, and other ingredients, and may also be produced to have various components and component concentrations depending on the cells to be cultured. In addition, commercially available plant-derived hydrolysates such as HyPep™ 7404, UltraPep™ Cotton, HyPep™ 7504, HyPep™ 4601N (Kerry, USA), Cotton 100, Cotton 200, Phytone™, and Soy 100 (Gibco, USA) may be used as a supplement, but the invention is not limited thereto.

The additive used to increase or decrease the N-glycan content of the glycoprotein used in the present invention is generally a component known to be involved in protein glycosylation. In particular, in order to limit the sialylation content, the delivery of sialic acid to the galactose residue should be limited, desialylation should be performed, or the galactosylation content should be limited. When culturing the cells, such additives, which are added to the medium at predetermined concentrations, include components as glycosylation precursors such as N-acetyl-D-mannosamine, glucose, mannose, glutamine and galactose, ammonia, and butyric acid.

Most animal cell cultures mainly use a medium containing serum. However, it is difficult to design a medium suitable for protein production because a medium containing serum is a complex composition, the chemical components of which are not elucidated clearly. A serum-free medium or a medium containing little serum is mainly used, because serum may have negative effects on separation and purification as well as problems associated with cost and reproducibility. Since the concentration of glucose, which is the carbon source, is very low in the serum-free medium, glucose is further added as a main carbon source to the medium for culture in order to maintain cell growth and produce a high concentration of the target protein, and glutamine may be further added thereto for culture. In particular, the sialylation level should be increased in order to increase the in-vivo half-life in the production of protein pharmaceuticals. For this purpose, glucose and glutamine in the medium should be maintained at certain concentrations or higher so as not to be depleted, and the pH of the culture medium should also be maintained at a specific level. The concentrations of glucose and glutamine measured in the culture medium refer to the concentrations of residual glucose and glutamine after consumption by the cells. In addition, promoters for improving the activity of enzymes associated with the increase of the sialylation level, or inhibitors for suppressing desialylation may be used. In addition, by adding precursors of N-glycans or controlling the activity promoters of related enzymes or culture conditions, the galactosylation level can be increased and thus the sialylation level can be also increased.

However, the N-glycan level cannot be controlled by the above method in the production of hyaluronidase PH20 or a variant thereof, whereas, when produced by the method according to the present invention, a hyaluronidase PH20 or a variant thereof that has desired glycan levels and high enzymatic activity can be produced.

The production method according to the present invention may further include separating and purifying the produced hyaluronidase PH20 or a variant thereof.

The separation and purification of the hyaluronidase PH20 or a variant thereof according to the present invention are preferably performed using not affinity binding, but the ionic bond and/or hydrophobic interaction characteristics of the hyaluronidase PH20 or variant thereof, but the invention is not limited thereto.

Specifically, the separation and purification of the hyaluronidase PH20 or a variant thereof according to the present invention are preferably performed using not affinity chromatography, but hydrophobic interaction chromatography and ion exchange chromatography, such as cation exchange chromatography and/or anion exchange chromatography, but the invention is not limited thereto.

In addition, the separation and purification of hyaluronidase PH20 or a variant thereof according to the present invention aims to remove the acidic hyaluronidase PH20 or a variant thereof having low enzymatic activity, and the removal of the acidic hyaluronidase PH20 or a variant thereof is preferably performed using ion exchange chromatography.

It is necessary to analyze the catalytic reaction rate of the enzyme in order to identify the industrial applicability of the enzyme. The enzymatic reaction may be classified into an enzymatic reaction having an active site having fixed reactivity and an enzymatic reaction having a plurality of active sites having different reactivity. It is known that the rate of catalytic reaction of an enzyme having a single active site having fixed reactivity, such as hyaluronidase, follows the Michaelis-Menten kinetics equation.

Michaelis-Menten enzyme kinetics are premised on the assumption of an enzymatic reaction as a two-step reaction system including a reversible reaction step in which Complex [ES] of Enzyme (E)-Substrate (S) is formed and an irreversible reaction in which the ES complex is dissociated to yield Product (P). In this case, $k_f$, $k_r$ and $k_{cat}$ are the rate constants of the reaction in each direction (Alan Fersht (1977). Enzyme structure and mechanism).

$$E + S \underset{k_r}{\overset{k_f}{\rightleftharpoons}} ES \overset{k_{cat}}{\longrightarrow} E + P$$

With regard to the enzymatic reaction, it is assumed that the process of reacting the enzyme with the substrate to produce the ES complex rapidly reaches equilibrium or a pseudo-steady state, assuming that $d[ES]/dt \approx 0$ is satisfied by sufficiently lowering the concentration of the enzyme by performing a reaction that maintains a sufficiently high substrate concentration. Since the kinetics formulas assuming fast equilibrium or pseudo-steady state are derived in the same manner, a pseudo-steady state in which the substrate concentration is initially higher than the enzyme concentration is assumed in most experiments.

When conditions such as "the amount of the enzyme is constant before and after the reaction" and "when a chemical reaction reaches chemical equilibrium, the reaction rate at which the product is obtained is equal to the rate at which the product is decomposed again" are adopted based on this assumption, the reaction rate of the final product may be expressed by the following Michaelis-Menten kinetics equation. In this case, $K_M = (k_r + k_{cat})/k_f$, and $V_{max} = k_{cat}[E]_0$.

$$v = \frac{d[P]}{dt} = \frac{V_{max}[S]}{K_M + [S]}$$

The Lineweaver-Burk equation is used to experimentally analyze the enzymatic reaction rate using the Michaelis-Menten kinetics equation. This equation shows relationship between the reciprocal 1/V of the experimentally measured reaction rate with the reciprocal 1/[S] of the given substrate concentration in the experiment. Statistical verification that this equation is a linear equation demonstrates that the enzymatic reaction is a reaction following the Michaelis-Menten kinetics equation, and $K_M$ and $V_{max}$ can be calculated using this equation.

Enzymes that catalyze a chemical reaction have a transition state after binding to a substrate at an active site, and the activation energy for reaching the transition state having high energy is lowered through multiple bonds with the substrate. The equilibrium constant for reaching this transition state is proportional to $k_{cat}/K_M$. Here, $1/K_M$ is an index that combines the extent to which an enzyme-substrate complex is produced by bonding the enzyme to the substrate with the extent to which the enzyme-substrate complex is maintained without being decomposed, and $k_{cat}$ is the equilibrium constant at which a product is obtained from the enzyme-substrate complex. Therefore, $k_{cat}/K_M$ can be said to be an indicator of how much product can be obtained from the substrate and the enzyme, that is, the catalytic efficiency of the enzyme.

The industrial availability of hyaluronidase is proportional to the enzyme catalytic efficiency thereof. In particular, when an enzyme is injected subcutaneously along with a polymeric pharmacologically active substance such as a monoclonal antibody, the enzyme catalytic efficiency of hyaluronidase plays an important role. In the case where the variant according to the present invention has higher $k_{cat}/K_M$ than wild-type PH20, when the hyaluronidase contained in the polymeric pharmacologically active substance is administered subcutaneously, hyaluronic acid present therein is rapidly decomposed, and thus a superior effect of rapidly dispersing the pharmacologically active substance can be obtained. In addition, when the variant according to the present invention has a greater $k_{cat}$ than the wild-type PH20, the maximum reaction rate $V_{max}$ increases at the same enzyme concentration, thereby providing excellent effects of decomposing a greater amount of hyaluronic acid during the same time period and dispersing the pharmacologically active substance across a wider region.

Therefore, in order to identify the enzymatic properties of the PH20 variant according to the present invention, the enzymatic reaction rate of each variant was analyzed, and $V_{max}$ (maximum enzymatic reaction rate), $K_m$ (substrate concentration under 50% $V_{max}$ condition), $k_{cat}$ (substrate conversion rate), and $k_{cat}/K_m$ (enzyme catalyst efficiency) thereof were compared in Example 4. The results demonstrate that the PH20 variant according to the present invention is superior to wild-type PH20.

Example

Hereinafter, the present invention will be described in more detail with reference to examples. However, it will be obvious to those skilled in the art that these examples are provided only for illustration of the present invention and should not be construed as limiting the scope of the present invention.

Example 1. Relationship Between Activity of Hyaluronidase, N-Glycan, and Isoelectric Focusing Pattern The results of analysis of the activity, isoelectric focusing pattern, and N-glycan level of the wild human hyaluronidase PH20 and the variant thereof, HM46, are shown in FIG. 1. Although the difference in the active units of the two hyaluronidases was more than two-fold, there was no great difference in the isoelectric point range or N-glycan level.

An experiment was conducted to identify the relationship between N-glycan, the isoelectric focusing pattern, and activity in hyaluronidase PH20. In the process of purifying the hyaluronidase PH20 variant, it was possible to separate a basic fraction (Fraction 1) from an acidic fraction (Fraction 2), and the respective fractions were used as samples. FIG. 2 shows the results of analysis of the isoelectric focusing pattern and enzymatic activity of the sample treated with PNGase F to remove all N-glycans, the sample treated with sialidase A to remove the terminal sialic acid, and the sample treated with sialidase A and galactosidase to remove the terminal sialic acid and galactose. The two fractions exhibited a difference with regard to the range of the isoelectric point, and the acidic fraction exhibited the decreased enzymatic activity. Upon treatment with PNGase F, the two fractions had no activity, and had a similar isoelectric focusing pattern. These results showed that the N-glycan level is closely related to enzymatic activity. Furthermore, it was found that there is a relationship between the content of sialic acid at the terminal and the enzymatic activity through the phenomenon whereby the isoelectric focusing pattern or enzymatic activity of the acidic fraction is similar to that of the basic fraction when removing sialic acid at the terminal. However, the basic fraction having a low terminal sialic acid content exhibited of improved enzymatic activity hyaluronidase compared to the acidic fraction having a high sialic acid content.

The relationship between the enzymatic activity and the N-glycan content was further demonstrated based on results of the evaluation of wild-type and a variety of variant hyaluronidases originating from different cell sources for culture.

TABLE 1

| Hyaluronidase type | Preparation | Relative activity | N-Glycan content | | |
|---|---|---|---|---|---|
| | | | Galacto-sylation (%) | Sialy-lation (%) | Manno-sylation (%) |
| Wild-type human PH20 | Temporary expression culture | 100% | 32.9 | 15.2 | 57.2 |
| Wild-type human PH20 | Cell line culture | 100% | 42.5 | 21.7 | 54.8 |
| HM46 | Temporary expression culture | 167% | 37.1 | 7.4 | 48.1 |
| HM46 | Cell line clone test culture #1 | 115% | 46.9 | 18.6 | 48.9 |
| HM46 | Cell line clone test culture #2 purified fraction #1 | 161% | 40.6 | 16.4 | 54.4 |
| HM46 | Cell line clone test culture#2 purified fraction #2 | 86% | 42.1 | 28 | 56.8 |
| HM46 | Cell line test culture #1 | 158% | 49.6 | 14.4 | 48.1 |
| HM46 | Cell line test culture #2 | 186% | 31.2 | 5.5 | 48.3 |
| HM46 | Cell line test culture #3 | 152% | 30.6 | 4 | 48.7 |
| HM46 | Cell line test culture #4 | 174% | 15.8 | 4.5 | 52.8 |
| HM46 | Cell line culture #1 | 170% | 14.8 | 2.8 | 49.9 |
| HM46 | Cell line culture #2 | 161% | 16.4 | 2.5 | 47.9 |
| HM46 | Cell line culture #3 | 162% | 17.9 | 4.4 | 49.1 |
| HM46 | Cell line culture #4 | 158% | 18.5 | 3.8 | 48.1 |
| Sheep PH20 | Temporary expression culture | 193% | 35.5 | 7.9 | 58.3 |
| Bonobo PH20 | Temporary expression culture | 72% | 38.7 | 18.8 | 55.5 |

Relative Activity: Activity Expressed as Percentage of (Activity of Sample)/(Activity of Wild Human PH20)

Galactosylation percentage (%): the sum of percentage (8) content of N-glycans containing galactose at the terminals, such as G1, G1F, G1F', G2, G2F, A1, A1F, A2, and A2F Sialylation percentage (%): the sum of percentage (%) content of N-glycans containing sialic acid at the terminals ends, such as A1, A1F, A2, and A2F.

Mannosylation percentage (%): the sum of percentage (%) content of N-glycans containing mannose at the terminals, such as M4G0F, M5, M5G0, M6, M7, M8, and M9.

The sequences of wild-type human PH20 and HM46 are disclosed in International Patent Publication No. 2020/022791.

Sheep PH20 and Bonobo PH20 samples were prepared by the method shown in Example 10, and the sequences are shown in Table 3.

As shown in Table 1, a variety of types of hyaluronidase PH20 and variant proteins were produced, and the N-glycan contents were investigated. For this purpose, a variety of cultures using different cell sources, such as a temporary expression culture produced by transfecting ExpiCHO cells with recombinant genes using ExpiFectamine CHO Reagent (Gibco, USA) every time culture was performed, a cell line clone culture using cell line clones produced using the recombinant genes, and a cell line culture using screened monoclones having high productivity were performed. Here, the cell line clone culture is a culture using highly productive cell line clones selected using selective markers from mammalian cell clones transfected with recombinant genes, is performed using a polyclonal cell line, and aims to produce monoclonal cell lines. The cell lines include a research cell bank (RCB), a production master cell bank (MCB), and a working cell bank (WCB). In addition, in the culture method, various combinations of test culture were tried to optimize production, and even here, it was found that there was a difference in activity and N-glycan.

Cell line clone test culture #1 is a 2 L batch culture performed at 37° C. without shift the culture temperature using HycellCHO medium (HyClone, USA). Cell line clone test culture #2 purified fraction #1 and cell line clone test culture #2 purified fraction #2 were fractions separated and purified by anion exchange chromatography from the harvested cell culture fluid cultured at 37° C. using a fed-batch method of containing EX-CELL® Advanced CHO fed-batch medium (Sigma-Aldrich, USA) in an 8 L batch with Cotton 100UF (Gibco) and then BalanCD® CHO Feed 4 (Irvine Scientific, USA), Purified fraction #1 is a low-salt elution fraction, and Purified fraction #2 is a high-salt elution fraction. Cell line test culture #1 was obtained by culturing at a culture temperature of 37° C. using a fed-batch method of containing EX-CELL® Advanced CHO fed-batch medium (Sigma-Aldrich, USA) in a 2 L batch with Cotton 100UF (Gibco) and then BalanCD® CHO Feed 4 (Irvine Scientific, USA), and then shifted the culture temperature to 32° C. when the integral viable cell density reached a predetermined level. Cell line test culture #2 was obtained by culturing at a culture temperature of 37° C. using a fed-batch method of containing EX-CELL® Advanced CHO fed-batch medium (Sigma-Aldrich, USA) in a 10 L batch with Cotton 100UF (Gibco, USA) and then CD CHO EfficientFeed™ B plus AGT™ (Gibco, USA), and then shifted the culture temperature to 32° C. when the integral viable cell density reached a predetermined level, followed by performing culture for 12 days. Cell line test culture #3 was obtained by culturing at a culture temperature of 37° C. using a fed-batch method of containing EX-CELL® Advanced CHO fed-batch medium (Sigma-Aldrich, USA) in a 50 L batch with Cotton 100UF (Gibco, USA) and then CD CHO EfficientFeed™ B plus AGT™ (Gibco, USA), and then shifted the culture temperature to 32° C. when the integral viable cell density reached a predetermined level. Cell line test culture #4 was obtained by culturing cells at a culture temperature of 37° C. using a fed-batch method of containing EX-CELL® Advanced CHO fed-batch medium (Sigma-Aldrich, USA) in a 10 L batch with Cotton 100UF (Gibco, USA) and then CD CHO EfficientFeed™ B plus AGT™ (Gibco, USA), followed by shifting the culture temperature to 32° C. when the integral viable cell density reached a predetermined level and culturing the cells for 13 days. Cell line culture #1, Cell line culture #2, Cell line culture #3, and Cell line culture #4 are obtained by culturing a research cell bank (RCB), a productive master cell bank (MCB), and a working cell bank (WCB) at a culture temperature of 37° C. using a fed-batch method of supplementing EX-CELL® Advanced CHO fed-batch medium (Sigma-Aldrich, USA) in a 200 L batch with Cotton 100UF (Gibco, USA) and then CD CHO EfficientFeed™ B plus AGT™ (Gibco, USA), followed by shifting the culture temperature to 32° C. when the integral viable cell density reached a predetermined level and culturing the cells for 12 days. Based on these conditions, experiments on the culture conditions of Examples 2 to 5 were conducted to establish a culture method for maintaining the N-glycan levels.

As can be seen from Table 1, wild human hyaluronidase PH20 and the variant thereof, and mammalian hyaluronidase PH20 should have a galactosylation level of 15 to 50%, a sialylation level of 2.5 to 28%, and a mannosylation level of 47 to 60% in the N-glycan, and should have a galactosylation level of 1 to 68%, a sialylation level of 1 to 38%, and a mannosylation level of 40 to 63% in the N-glycan when applying a 95% confidence interval to the test results, in order to impart industrially useful hyaluronidase activity thereto. Such numerical values may also include an error of 10% because there is a variation upon measurement of the glucose levels in proteins, depending on conditions such as the equipment used for the experiment, the enzymatic reaction time, the test temperature, the proficiency of the tester, and the like, so the glucose level measured in the present invention should be interpreted in a broader sense in consideration of variation between laboratories, rather than in a limited sense.

Moreover, in particular, taking into consideration the relationship between activity and sialylation, it can be seen that hyaluronidase having activity higher than the activity of wild human PH20 and thus being industrially useful can be produced only when sialylation is limited to about 30% or less. The above numerical value may be derived as the result of experimentation, and may include an error of 10%.

The high-quality hyaluronidase maintaining the N-glycan level was identified by temporary expression culture, and cell lines were produced by selecting monoclonal strains having high productivity for stable commercial production. All of Cell line test cultures #2, #3, #4, and Cell line cultures #1, #2, #3, #4 shown in Table 1, which are obtained by culture methods using the results of Examples 2, 3, 4 and 5, exhibited an enzyme expression level of 10,000 unit/mL or more, suggesting the possibility of producing high-quality hyaluronidase at high efficiency and low cost.

Example 2. Culture Dependent Upon Additive

A hyaluronidase PH20 variant was inoculated at $2 \times 10^6$ cells/mL into each of three 125 mL Erlenmeyer flasks containing EX-CELL® Advanced CHO fed-batch medium (Sigma-Aldrich, USA) supplemented or not supplemented with Cotton 200UF (Gibco, USA) and then 20 mM N-acetyl-D-mannosamine (NZP, Netherlands) or 50 mM galactose (Pfanstiehl, USA), cultured by batch culture in an incubator at 37° C. and 8% $CO_2$ and then fed-batch cultured at a decreased temperature of 32° C. when the integral viable cell density (IVCD) reached a shift range. The feed medium, CD CHO EfficientFeed™ B plus AGT™ medium (Gibco, USA), was supplied daily in an amount of 1.88% of the culture starting volume in the flask. Cell samples were collected daily from the cell culture fluids, and the viable cell density, cell viability, pH, and lactate levels were measured. After termination of culture, centrifugation was performed at 2,000 rpm for 10 minutes to obtain a culture supernatant. The activity of the sample cultured under the above conditions was identified by HPLC and turbidity analysis, and protein patterns and N-glycan levels were observed by isoelectric focusing and glycosylation analysis. The medium supplemented with 50 mM galactose exhibited a 24% increase in galactosylation and a 2% decrease in activity compared to the medium not supplemented with 50 mM galactose, and the medium supplemented with 20 mM N-acetyl-D-mannosamine exhibited a 35% increase in sialylation and a 20% decrease in activity compared to the medium not supplemented with 20 mM N-acetyl-D-mannosamine (FIGS. 3, 4, 5, and 6).

Example 3. Culture Dependent Upon Culture Period

Cells overexpressing the hyaluronidase PH20 variant were inoculated at $2\times10^6$ cells/mL into EX-CELL® Advanced CHO Fed-Batch medium (Sigma-Aldrich, USA) in a Sartorius 200 L bioreactor. On the second day of culture, fed-batch culture was performed using Cotton 200UF (Gibco, USA) and CD CHO EfficientFeed™ B plus AGT™ medium (Gibco, USA), which is a concentrated nutrient medium (Gibco, USA), as a feed medium, cultured at a pH of 7.2±0.4 and DO of 40% at a rate of 47 rpm. Initial culture was performed at 37° C., the temperature was shifted to 32° C. when the integral viable cell density reached the change range, and fed-batch culture was performed. The feed medium, CD CHO EfficientFeed™ B plus AGT™ medium (Gibco, USA), was supplied daily in an amount of 1.88% of the culture starting volume in 200 L bioreactor. With respect to the culture period, the culture was terminated on the 19th day after culture, at which time the cell viability had dropped to 40% or less. A variety of cell samples were collected daily from the cell culture fluids, the viable cell density, cell viability, integral viable cell density, and ammonium ion level were measured, and the cultured solution was harvested using a depth filter. The activity of the samples cultured under the above conditions was identified by HPLC and turbidity analysis, and protein patterns and N-glycan levels were observed by isoelectric focusing and glycosylation analysis. As the number of days of culture increased, the galactosylation and sialylation levels decreased and the activity increased (FIGS. 7, 8, 9, and 10).

Example 4. Culture Under Controlled Glucose Concentration in Culture Medium

Cells overexpressing the hyaluronidase PH20 variant were inoculated at $2\times10^6$ cells/mL into EX-CELL® Advanced CHO Fed-Batch medium (Sigma-Aldrich, USA) in a Sartorius 2 L bioreactor. On the second day of culture, fed-batch culture was performed using Cotton 200UF (Gibco, USA) and CD CHO EfficientFeed™ B plus AGT™ medium (Gibco, USA), which is a concentrated nutrient medium (Gibco, USA) as a feed medium, cultured at a pH of 7.2±0.4 and DO of 40% at a rate of 120 rpm. Initial culture was performed at 37° C., the temperature was shifted to 32° C. when the integral viable cell density reached the change range, and fed-batch culture was then performed. The feed medium, CD CHO EfficientFeed™ B plus AGT™ medium (Gibco, USA), was supplied daily in an amount of 1.88% of the culture starting volume in the 2 L bioreactor. A variety of cell samples were collected daily from cell culture fluids, and viable cell density, cell viability, pH, osmolality, and glucose and lactate concentration were measured.

The concentration of glucose in the culture medium was measured daily and was controlled from the point in time at which the concentration of glucose contained in the culture supernatant was not more than the reference concentration of 2, 4, or 6 g/L as the glucose was consumed by growing cells. When the measured glucose concentration was 2, 4, or 6 g/L or less, which are respective standard concentrations, 200 g/L glucose stock solution was added for a maximum time of 3 hours in an amount so as to reach the standard concentration. When the measured glucose concentration was 2, 4, or 6 g/L or more, no stock solution was added to maintain each standard concentration. In general, the effect of changes in glucose content on cell growth is negligible within 3 hours during mammalian cell culture.

In this case, the condition of maintaining 2 g/L as the reference concentration was referred to as a 1 g/L (+1 g/L) concentration condition, the condition of maintaining 4 g/L as the reference concentration was referred to as a 3 g/L (+1 g/L) concentration condition, and the condition of maintaining 6 g/L as the reference concentration was referred to as a 5 g/L (+1 g/L) concentration condition. For example, the condition for maintaining the glucose concentration of 1 g/L (+1 g/L) means that the lower limit of the control range of glucose concentration is set to 0 g/L and the upper limit of the control range of glucose concentration is set at 2 g/L, and means that, in actual culture, when the measured glucose concentration in the culture supernatant reaches the lower limit of 0 g/L, 200 g/L of a glucose stock solution was further added so that the maximum glucose concentration reached 2 g/L, and when the glucose concentration in the culture supernatant reached the upper limit of 2 g/L, 200 g/L of a glucose stock solution was not added. Therefore, in the two concentration conditions, namely, the 1 g/L (+1 g/L) concentration and the 3 g/L (+1 g/L) concentration, the concentration condition of 2 g/L corresponds to the upper limit with respect to the 1 g/L (+1 g/L) concentration condition and corresponds to the lower limit with respect to the 3 g/L (+1 g/L) concentration condition, so the two conditions are conditions at which completely different actions occur, and thus are not considered to overlap each other.

After termination of the culture, the culture supernatant was obtained by centrifugation at 4° C. and 10,000 rpm for 60 minutes. The activity of the sample cultured under the above conditions was identified by HPLC and turbidity analysis, and protein patterns and N-glycan levels were identified by focusing isoelectric and glycosylation analysis. The results showed that as the concentration of glucose in the culture supernatant increased, the levels of galactosylation and sialylation increased and the activity decreased (FIGS. 11, 12, 13 and 14).

Example 5. Culture at Controlled pH

Cells overexpressing the hyaluronidase PH20 variant were inoculated at $2\times10^6$ cells/mL into EX-CELL® Advanced CHO Fed-Batch medium (Sigma-Aldrich, USA) in a Sartorius 2 L bioreactor. On the second day of culture, a fed-batch culture was performed using Cotton 200UF (Gibco, USA) and CD CHO EfficientFeed™ B plus AGT™ medium (Gibco, USA), which is a concentrated nutrient medium (Gibco, USA) as a feed medium, cultured at a DO of 40% at a rate of 120 rpm. Initial culture was performed at 37° C., the temperature was shifted to 32° C. when the integral viable cell density reached the change range, and fed-batch culture was then performed. The feed medium, CD CHO EfficientFeed™ B plus AGT™ medium (Gibco, USA), was supplied daily in an amount of 1.88% of the culture starting volume in the 2 L bioreactor. The culture temperature was shifted and the culture was divided and further cultured according to four pH conditions, namely pH 6.8±0.1, pH 7.0±0.1, pH 7.2±0.1, and pH 7.4±0.1, in order to find improved conditions compared to the conventional pH 7.2±0.4. The pH control range of the culture was set according to these four conditions using a conventional bioreactor that includes a pH control function. For example, pH 7.0±0.1 means that the lower limit of the pH control range is pH 6.9, and the upper limit of the pH control range is pH 7.1. In actual culture, when the pH of the culture medium reaches the lower limit of pH 6.9, a base is added to elevate the pH, and when the pH of the culture medium reaches the upper limit of pH 7.1, carbon dioxide is added to lower the pH. Therefore, in the two conditions of pH 6.8±0.1 and pH 7.0±0.1, the condition of pH 6.9 corresponds to the upper limit at pH 6.8±0.1, and to the lower limit at pH 7.0±0.1. Therefore, the two conditions are considered not to overlap each other. Culture was performed up to the day of culture at which the cell viability was 40% or less, multiple cell samples were collected daily from the cell culture fluids, and the viable cell density, cell viability, pH, and integral viable cell density level were measured. After termination of the culture, the culture supernatant was obtained by centrifugation at 4° C. and 10,000 rpm for 60 minutes. The activity of the sample cultured under the above conditions was identified by HPLC and turbidity analysis, and protein patterns were identified by isoelectric focusing. The activity changed depending on the pH of the culture medium, and the highest activity and the lowest sialylation level were observed at a pH of 7.0±0.1, which was an improved condition compared to the conventional condition (Table 2, FIGS. 15, 16, and 17).

TABLE 2

| N-Glycan pattern | pH 7.2 ± 0.4 (Conventional condition) | pH 6.8 ± 0.1 | pH 7.0 ± 0.1 | pH 7.2 ± 0.1 | pH 7.4 ± 0.1 |
| --- | --- | --- | --- | --- | --- |
| Galactosylation (%) | 39.6 | 49.4 | 37.0 | 42.1 | 47.6 |
| Sialylation (%) | 14.6 | 12.7 | 6.3 | 13.9 | 20.9 |
| Mannosylation (%) | 48.4 | 43.3 | 50.5 | 50.3 | 49.3 |
| Total afucosylation (%) | 53.4 | 46.2 | 51.2 | 56.2 | 57.2 |
| Afucosylation (%) | 7.7 | 5.9 | 4,2 | 8.9 | 10.7 |
| Relative Specific activity (%) | 100% | 92% | 115% | 104% | 98% |

Example 6. Purification of Hyaluronidase Using Animal Cell Culture Supernatant

Step 1: Treatment of Culture Supernatant with Buffer Exchange/Surfactant

The conditions of culture solutions were readjusted to the first anion exchange column equilibration conditions through control of pH and conductivity by UF/DF using a 30 kDa MWCO membrane filter. The readjusted solution was treated with an appropriate concentration of solvent/surfactant for viral inactivation, and reacted at room temperature for about 60 minutes.

Step 2: Primary Anion Exchange (Q Sepharose Fast Flow) Column Chromatography

The filtered protein solution was passed through a primary anion exchange column to capture hyaluronidase through an anion exchange resin and was eluted from the column at a high salt concentration. Prior to loading, the column was equilibrated using a tromethamine buffer (having a pH of 8.0 and a salt concentration of 30 mM). After loading, the column was washed using the same buffer (primary washing). After the primary washing, the column was secondarily washed with the same buffer (having a pH of 8.0, but having a salt concentration of 60 mM, having higher conductivity than that of the salt concentration in the primary washing). After the secondary washing, elution of the desired protein, hyaluronidase, was performed using an appropriate buffer having a pH of 8.0 and a 200 mM salt concentration, as shown in FIG. 18.

Step 3: Secondary Anion Exchange (Capto Q) Column Chromatography

The filtered protein solution was passed through a secondary anion exchange column to remove the acidic variant of hyaluronidase with an anion exchange resin, and was eluted from the column at a high salt concentration. Prior to loading, the column was equilibrated using a Bistris buffer (having a pH of 6.0 and having no salt). After loading, the column was washed using the same Bistris buffer (primary washing). After the primary washing, the column was washed with the same Bistris buffer, which had a salt concentration of 20 mM, having higher conductivity than that of the salt concentration in the primary washing). After the secondary washing, elution of the desired protein, hyaluronidase, was performed using a Bistris buffer having a salt concentration as shown in FIG. 19.

Step 4: Cation Exchange (Capto MMC) Column Chromatography

The readjusted protein solution was passed through a cation exchange column to remove the acidic variant of hyaluronidase with a cation exchange resin, and was eluted from the column at a high salt concentration. Prior to loading, the column was equilibrated using a pH 5.5 citrate buffer having a salt concentration of 80 mM. After loading, the column was washed using the same citrate buffer (primary washing). After the primary washing, the column was washed with an appropriate pH 7.5 Bistris buffer. After the secondary washing, elution of the desired protein, hyaluronidase, was performed using a pH 8.0 Bistris buffer having a salt concentration of 400 mM, as shown in FIG. 20.

Step 5: Nano-Filtration/Formulation

After the cation exchange column step, the protein solution containing the desired hyaluronidase was filtered through a 1 um filter and subjected to nano-filtration. The nano-filtered protein solution was concentrated to a high concentration of 10 mg/mL and readjusted by UF/DF using an 8 kDa MWCO membrane filter for exchange with a pH 7.0 histidine buffer containing a 145 mM salt.

Example 7. Analysis of Enzymatic Activity of Hyaluronidase

The enzymatic activity of hyaluronidase PH20 and other hyaluronidases was measured using a turbidimetric assay as follows.

A turbidimetric assay is a method of measuring the precipitate produced during mixing of hyaluronic acid with albumin (BSA) using absorbance. When hyaluronic acid is hydrolyzed by PH20, the absorbance decreases during mixing with albumin. In general, this process was performed as follows. Hyaluronidase PH20 (Sigma) was diluted to 1, 2, 5, 7.5, 10, 15, 20, 30, 50, or 60 units/mL and placed in respective tubes. The purified protein sample was dissolved in enzyme diluent buffer (20 mM Tris·HCl, pH 7.0, 77 mM NaCl, 0.01% (w/v) bovine serum albumin) and diluted 100×, 300×, 600×, 1200×, or 2400× in each tube. 3 mg/mL of a hyaluronic acid solution was diluted 10× to 0.3 mg/mL in other tubes, to adjust the volume of each tube to 180 μl. 60 μl of the enzyme was mixed with the diluted hyaluronic acid solution and reacted at 37° C. for 45 minutes. After the reaction, 50 μl of the reacted enzyme and 250 μl of an acidic albumin solution were added to each well in a 96-well plate and shaken for 10 minutes, and absorbance was measured at 600 nm using a spectrophotometer. The active unit of the sample was obtained using the test results of a standard product, the active unit of which is known, and the test results of the sample.

Example 8. Isoelectric Focusing Analysis of Hyaluronidase

Isoelectric focusing of hyaluronidase was analyzed using a precast gel (pH 3-7, Invitrogen) and a buffer solution for isoelectric focusing. The purified hyaluronidase sample was loaded on the precast gel, and the precast gel was run using an electrophoresis apparatus produced by Novex Corporation at 100V for 1 hour, at 200V for 1 hour, and at 500V for 30 minutes. After the running was completed, the gel was washed with purified water, and the protein was fixed with a 12% TCA solution, stained with Coomassie Blue R-250 staining solution, and bleached with an acetic acid-methanol solution to assay the protein bands shown on the gel.

Example 9. Analysis of N-Glycan Level of Hyaluronidase

The N-glycan level of hyaluronidase was analyzed by labeling the N-glycan sample, separated by treating hyaluronidase with PNGase F (N-glycosidase F), with 2-AB (2-aminobanzamide), followed by performing ultrahigh-performance liquid chromatography using an ACQUITY UPLC Glycan BEH Amide column (Waters). The purified hyaluronidase sample was desalted and reacted with PNGase F at 37° C. for 16 to 18 hours to separate N-glycan therefrom. The N-glycan was labelled with 2-AB and then reacted at 65° C. for 3 hours, and excess 2-AB was removed therefrom. The labeled N-glycan sample was separated by HPLC with a 72%-20% acetonitrile gradient. The separated sample was detected with a fluorescence detector (FLD) to analyze the N-glycan levels. The respective separated N-glycans were classified, N-glycans containing galactose at the terminal thereof (G1, G1F, G1F', G2, G2F, A1, A1F, A2, A2F and the like) were added up to determine a galactosylation percentage (%) level, N-glycans containing sialic acid at the terminal thereof (A1, A1F, A2, A2F and the like) were added up to determine a sialylation percentage (%) level, and N-glycans containing mannose at the terminal thereof (M4G0F, M5, M5G0, M6, M7, M8, M9 and the like) were added up to determine a mannosylation percentage (%) level.

Example 10. Preparation of Animal-Derived Hyaluronidase and Analysis of N-Glycan Level (1) Production of Bonobo and Sheep Hyaluronidase PH20 Genes In order to investigate the activity and N-glycan level of hyaluronidase PH20 of an animal-derived anthropoid, that is, bonobo, and Artiodactyla, that is, sheep, hyaluronidase PH20 was prepared as follows. CDNA was synthesized from wild-type genes, and was inserted into the Xho I and Not I restriction enzyme sites of pcDNA3.4-TOPO vector. For expression in ExpiCHO cells, one of the signal peptides of human growth hormone, human serum albumin, or human Hyal1 was used as a signal peptide, instead of the native signal peptide of PH20. For protein purification using a HisTrap column, a His-tag DNA sequence was positioned at the 3'-terminal of the PH20 cDNA. Each sequence was identified using DNA sequencing. Table 3 shows the sequences of animal-derived hyaluronidases. Table 3

TABLE 3

| Animal-derived hyaluronidase | Amino acid sequence |
|---|---|
| Sheep PH20 | LDFRAPPLISNTSFLWAWNAPAERCVKIFKLPPDLRLFSVKGSP<br>QKSATGQFITLFYADRLGYYPHIDEKTGNTVYGGIPQLGNLKN<br>HLEKAKKDIAYYIPNDSVGLAVIDWENWRPTWARNWKPKDV<br>YRDESVELVLQKNPQLSFPEASKIAKVDFETAGKSFMQETLKL<br>GKLLRPNHLWGYYLFPDCYNHNYNQPTYNGNCSDLEKRRND<br>DLDWLWKESTALFPSVYLNIKLKSTPKAAFYVRNRVQEAIRLS<br>KIASVESPLPVFVYHRPVFTDGSSTYLSQGDLVNSVGEIVALG<br>ASGIIMWGSLNLSLTMQSCMNLGNYLNTTLNPYIINVTLAAK<br>MCSQVLCHDEGVCTRKQWNSSDYLHLNPMNFAIQTGKGGKY<br>TVPGKVTLEDLQTFSDKFYCSCYANINCKKRVDIKNVHSVNV<br>CMAEDICIEGPVKLQPSDH (SEQ ID NO: 1) |
| Bonobo PH20 | LNFRAPPVIPNVPFLWAWNAPSEFCLGKFDEPLDMSLFSFIGSP<br>RINVTGQDVTIFYVDRLGYYPYIDSITGVTVNGGIPQKISLQDH<br>LDKAKKDITFYMPVDNLGMAVIDWEEWRPTWARNWKPKDI<br>YKNRSIELVQQQNVQLNLTEATEKAKQEFEKAGKDFLVETIK<br>LGKLLRPNHLWGYYLFPDCYNHHYKKPGYNGSCFNVEIKRN<br>DDLSWLWNESTALYPSIYLNTQQSPVAATLYVRNRVREAIRV<br>SKIPDAKSPLPVFVYTRIVFTDQVLKFLSQDELVYTFGETVALG<br>ASGIVIWGTLSIMRSMKSCLLLDNYMETILNPYIINVTLAAKM<br>CSQVLCQEQGVCIRKNWNSSDYLHLNPDNFAIQLEKGGKFTV<br>RGKPTLEDLEQFSEKFYCSCYSTLSCKEKADVKDTDAVDVCIA<br>DGVCIDAFLKPPMETEESQIFY (SEQ ID NO: 2) |

(2) Bonobo and Sheep Hyaluronidase PH20 Expression

Expression was performed using the ExpiCHO expression system. When the number of ExpiCHO cells reached $6\times10^6$ cells/mL, the ExpiCHO cells were transfected using ExpiFectamine CHO reagent with a plasmid in which hyaluronidase PH20 cDNA was inserted into pcDNA3.4-TOPO vector. The cell culture medium used herein was an ExpiCHO expression medium (100~500 mL). After transfection, the ExpiCHO cells were cultured while shaking at 130 rpm for a total of 6 days. During this period, the cells were cultured at 37° C. for 1 day, and were then further cultured at a lowered temperature of 32° C. for 5 days. Upon completion of the culture, the cells were centrifuged at 10,000 rpm for 30 minutes to obtain a cell supernatant.

(3) Purification of Bonobo and Sheep Hyaluronidase PH20

The C-terminal His-tag-attached animal-derived hyaluronidase recombinant proteins, produced in the ExpiCHO cells, were purified through two-step column chromatography using an AKTA prime system (GE Healthcare Systems). The bonobo PH20 has a pI of 6, so Q Sepharose for anion exchange chromatography was used therefor, and the sheep PH20 has a pI of 8 or more, and thus was subjected to one-step purification using a Capto S column for cation exchange chromatography. Each protein was subjected to two-step purification using a HisTrap HP column for His-Tag affinity chromatography.

For protein purification using the Q Sepharose column, buffer A (20 mM sodium phosphate, pH 7.5) and buffer B (20 mM sodium phosphate, pH 7.5, 0.5 M NaCl) were prepared. The protein was bound to the Q Sepharose column, and the column was flushed with 5 CV of buffer A to remove nonspecifically bound proteins, and was then flushed with 5 CV of buffer B at a concentration gradient from 0 to 100% to elute the protein.

For protein purification using the Capto S column, buffer A (20 mM sodium phosphate, 15 mM NaCl, pH 6.0) and buffer B (20 mM sodium phosphate, 500 mM NaCl, pH 6.0) were prepared. The pH and conductivity of the culture medium were adjusted to be the same as those of buffer A, and the culture medium was filtered through a membrane having a pore size of 0.22 μm. The protein sample was bound to the Capto S column, and the column was flushed with 3 column volume (CV) of buffer A to remove nonspecifically bound proteins. The column was flushed with 4 CV of buffer B to elute the protein.

For protein purification using the HisTrap HP column, buffer A (20 mM sodium phosphate, 500 mM NaCl, pH 7.5) and buffer B (20 mM sodium phosphate, 500 mM NaCl, 500 mM imidazole, pH 7.5) were prepared. The protein sample was bound to the HisTrap HP column, and the column was flushed with 7 CV of 7% buffer B to remove nonspecifically bound proteins, and was then flushed with 3 CV of 40% buffer B to elute the target protein. The column eluate was dialyzed using a dialysis buffer (20 mM sodium phosphate, 100 mM NaCl, pH 7.0).

(4) Bonobo and Sheep PH-20 Hyaluronidase Analysis

Activity analysis was performed in the same manner as in Example 7, and N-glycan level analysis was performed in the same manner as in Example 9. The results are shown in Table 1.

Example 11. Enzyme Kinetics Analysis of Variants Depending on N-Glycan Level

In order to analyze the enzyme kinetics of the variants according to the present invention, the enzymatic activity was measured by the Morgan-Elson method (Takahashi, T. et al (2003) Anal. Biochem. 322:257-263). The Morgan-Elson method is a colorimetric method that assays red substances (at 545 nm) produced by a reaction at the reduced terminal of N-acetyl-D-glucosamine (GlcNAc), produced upon hydrolysis of hyaluronic acid by hyaluronidase, with para-dimethylaminobenzaldehyde (DMAB), that is, Ehrlich's Reagent. N-acetyl-D-glucosamine (GlcNAc, Sigma) diluted to 0.25, 0.50, 0.75, 1.00 or 1.25 mM in a dilution buffer solution (0.1 M NaPi, 0.1 M NaCl, 1.5 mM saccharic acid 1,4-lactone, pH 5.35) was reduced by treatment with tetraborate in each test tube, and then DMAB was added to induce a colorimetric reaction. After the reaction, absorbance was measured at 545 nm to create a standard reaction curve for GlcNAc. Hyaluronic acid as a substrate was diluted to 0.54, 0.65, 0.87, 1.23, or 2.17 UM in a dilution buffer solution in each test tube, and hyaluronidase was added to each test tube, followed by reaction at 37° C. for 5 minutes and heating at 100° C. for 5 minutes to complete the enzymatic reaction. The result was reduced by treatment with tetraborate, and DMAB was added to induce a colorimetric reaction. After the reaction, absorbance was measured at 545 nm, and enzymatic activity was measured using the standard reaction curve of GlcNAc above. The enzyme kinetics of the wild-type PH20 of SEQ ID NO: 1 and the PH20 variant according to the present invention were analyzed using this method. As a result, the Lineweaver-Burk curve was found to be linear, which means that the PH20 variant according to the present invention follows the Michaelis-Menten enzyme kinetics formula.

Table 4 shows results of analysis of the enzyme kinetics of fractions #1 and #2 obtained from Cell line clone test culture #2, among the samples in Table 1 of Example 1. The results showed that when the galactosylation and mannosylation levels fall within similar ranges and the sialylation level is low, the enzymatic activity of the recombinant hyaluronidase is increased due to the high catalytic efficiency ($k_{cat}/K_m$) of the enzyme.

The experimental result proves that the activity of an enzyme having the same amino acid structure may be affected by the change in glycosylation, more specifically, by the change in the sialylation level. Therefore, this suggests that, in an attempt to produce industrially useful hyaluronidase by mass-producing wild PH20 hyaluronidase or a variant thereof using a recombinant method, an enzyme having greater industrial applicability can be developed by controlling the sialyation level.

TABLE 4

| Hyaluronidase type | Preparation | Relative activity | N-glycan content | | | $K_M$ (μM) | $k_{cat}$ (1/sec) | $k_{cat}/K_M$ (sec/μM) |
| | | | Galactosylation (%) | Sialylation (%) | Mannosylation (%) | | | |
|---|---|---|---|---|---|---|---|---|
| HM46 | Cell line clone | 161% | 40.6 | 16.4 | 54.4 | 1.11 ± 0.07 | 47.6 ± 3.8 | 42.7 ± 0.7 |

TABLE 4-continued

| Hyaluronidase type | Preparation | Relative activity | N-glycan content Galactosylation (%) | Sialylation (%) | Mannosylation (%) | $K_M$ (μM) | $k_{cat}$ (1/sec) | $k_{cat}/K_M$ (sec/μM) |
|---|---|---|---|---|---|---|---|---|
| HM46 | test culture #2 purified fraction #1 Cell line clone test culture #2 purified fraction #2 | 86% | 42.1 | 28.0 | 56.8 | 1.05 ± 0.15 | 33.9 ± 4.9 | 32.4 ± 0.1 |

INDUSTRIAL APPLICABILITY

The method for producing a recombinant hyaluronidase PH20 protein or a variant thereof according to the present invention enables production of a recombinant hyaluronidase PH20 protein or a variant thereof having high productivity and high enzymatic activity, and thus realizes mass-production and supply of the recombinant hyaluronidase PH20 protein or a variant thereof.

Although specific configurations of the present invention have been described in detail, those skilled in the art will appreciate that this detailed description is provided as preferred embodiments for illustrative purposes only, and should not be construed as limiting the scope of the present invention. Therefore, the substantial scope of the present invention is defined by the accompanying filed claims and equivalents thereto.

REFERENCES

1. L. H. Bookbinder, A. Hofer, M. F. Haller, M. L. Zepeda, G-A. Keller, J. E. Lim, T. S. Edgington, H. M. Shepard, J. S. Patton, G. I. Frost. (2006). A recombinant human enzyme for enhanced interstitial transport of therapeutics. J. Control. Release. 114, 230-241.
2. Douglas B. Muchmore, M.D., and Daniel E. Vaughn, Ph.D. (2012). Accelerating and Improving the Consistency of Rapid-Acting Analog Insulin Absorption and Action for Both Subcutaneous Injection and Continuous Subcutaneous Infusion Using Recombinant Human Hyaluronidase. J. Diabetes Sci. and Technol. 6 (4): 764-72
3. E. M. Krantz. (1980). Low-dose intramuscular ketamine and hyaluronidase for induction of anaesthesia in non-premedicated children. S. Afr. Med. J. 58 (4): 161-2.
4. W. A. Clement, S. H. Vyas, J. N. Marshall, J. H. Dempster. (2003). The use of hyaluronidase in nasal infiltration: prospective randomized controlled pilot study. J. Laryngol. Otol. 117(8): 614-8.
5. Thomas J. R., Wallace M. S., Yocum R. C., Vaughn D. E., Haller M. F., Flament J. (2009). The INFUSE-Morphine study: use of recombinant human hyaluronidase (rHuPH20) to enhance the absorption of subcutaneously administered morphine in patients with advanced illness. J. Pain and Symptom Manag. 38 (5): 663-672.
6. George Harb, Francois Lebel, Jean Battikha, Jeffrey Thackara. (2010). Safety and pharmacokinetics of subcutaneous ceftriaxone administered with or without recombinant human hyaluronidase (rHuPH20) versus intravenous ceftriaxone administration in adult volunteers. Curr. Med. Res. Opin. 26(2):279-88.
7. Richard L. Wasserman. (2014). Overview of recombinant human hyaluronidase-facilitated subcutaneous infusion of IgG in primary immunodeficiencies. Immunotherapy. 6(5):553-67.
8. Harris R. J., Shire S. J., Winter C. (2004). Commercial manufacturing scale formulation and analytical characterization of therapeutic recombinant antibodies. Drug. Dev. Res. 61:137-154.
9. Stephan Schilling, Torsten Hoffmann, Fred Rosche, Susanne Manhart, Claus Wasternack, and Hans-Ulrich Demuth. (2002). Heterologous Expression and Characterization of Human Glutaminyl Cyclase: Evidence for a Disulfide Bond with Importance for Catalytic Activity. Biochemistry, 35, 10849-10857.
10. H. Tachibana 1, K. Taniguchi, Y. Ushio, K. Teruya, K. Osada, H. Murakami. (1994). Changes of monosaccharide availability of human hybridoma lead to alteration of biological properties of human monoclonal antibody. Cytotechnology. 16(3): 151-7.
11. Veronica Restelli, Ming-Dong Wang, Norman Huzel, Martin Ethier, Helene Perreault, Michael Butler. (2006). The effect of dissolved oxygen on the production and the glycosylation profile of recombinant human erythropoietin produced from CHO cells. Biotechnol. Bioeng. 94: 481-494.
12. M. C. Borys, D. I. Linzer, E. T. Papoutsakis. (1993). Culture pH affects expression rates and glycosylation of recombinant mouse placental lactogen proteins by Chinese hamster ovary (CHO) cells. Biotechnology (NY). 11: 720-724.
13. M. C. Borys, D. I. Linzer, E. T. Papoutsakis. (1994). Ammonia affects the glycosylation patterns of recombinant mouse placental lactogen-I by Chinese hamster ovary cells in a pH-dependent manner. Biotechnol. Bioeng. 43:505-514.
14. Clark K. J., Chaplin F. W., Harcum S. W. (2004). Temperature effects on product quality-related enzymes in batch CHO cell cultures producing recombinant tPA. Biotechnol. Prog. 20:1888-1892.
15. Arming S., Strobl B., Wechselberger C., Kreil G. (1997) In-vitro mutagenesis of PH-20 hyaluronidase from human sperm. Eur J. Biochem. 247:810-814

What is claimed is:

1. A method for producing a recombinant protein that comprises at least one of hyaluronidase PH20 or a variant thereof, the method comprising:
    first culturing host animal cells expressing the recombinant protein until an integral viable cell density of the host animal cells reaches 20×10⁶ to 120×10⁶ cells×day/mL, wherein first culturing is performed within a first temperature range from 35° C. to 38° C.; and
    subsequently second culturing at least part of the host animal cells from first culturing for 2 to 18 days, which produces the recombinant protein, wherein second culturing is performed within a second temperature range from 28° C. to 34° C.,
    wherein the second culturing maintains (a) a residual glucose concentration within a range from 0.001 g/L to 4.5 g/L and/or (b) pH within a range from 6.8 to 7.2 in a culture medium therefor,
    wherein sialylation of N-glycan of the produced recombinant protein is 1 to 38%, and
    wherein the produced recombinant protein has a hyaluronidase enzymatic activity at 10,000 units/mL or higher.

2. The method according to claim 1, wherein galactosylation of N-glycan is 1 to 68%, and mannosylation of N-glycan is 40 to 63%.

3. The method according to claim 1, wherein sialylation of N-glycan is 1 to 30%.

4. The method according to claim 1, wherein the recombinant protein has a specific enzymatic activity as hyaluronidase at least 10% higher than a specific enzymatic activity of a wild human PH20.

5. The method according to claim 1, wherein at least one of the first culturing or the second culturing are performed by one or more methods selected from the group consisting of batch culture, repeated batch culture, fed-batch culture, repeated fed-batch culture, continuous culture, and perfusion culture.

6. The method according to claim 1, wherein at least one of the first culturing or the second culturing are performed under one or more conditions selected from the group consisting of:
    (i) a condition in which an ammonia concentration is maintained at 5 mM or higher in a culture medium thereof;
    (ii) a condition in which one or more substances is added to the culture medium thereof, wherein the one or more substances are selected from the group consisting of glutamine, glucosamine, uridine, glucosamine, and sodium butyrate; and
    (iii) a condition in which galactose and manNAc are not added to the culture medium thereof.

7. The method according to claim 1, wherein the recombinant protein comprises substitution of one or more amino acid residues when compared to an amino acid sequence of a wild human PH20.

8. The method according to claim 1, further comprising separating and purifying the produced recombinant protein.

9. The method according to claim 8, wherein separating and purifying the produced recombinant protein are performed using ionic bond and/or hydrophobic interaction characteristics thereof, rather than affinity binding.

10. The method according to claim 9, wherein separating and purifying the recombinant protein are performed using hydrophobic interaction chromatography and ion exchange chromatography, rather than affinity chromatography.

11. The method according to claim 8, wherein purifying further comprises removing at least part of acidic recombinant protein.

12. The method according to claim 11, wherein removing the acidic recombinant protein uses ion exchange chromatography.

13. The method according to claim 7, wherein the recombinant proteinfurther comprises truncation of at least one amino acid residue of N-terminus when compared to an amino acid sequence of a wild human PH20.

14. The method according to claim 7, wherein the recombinant protein further comprises truncation of at least one amino acid residue of C-terminus when compared to an amino acid sequence of a wild human PH20.

15. The method according to claim 7, wherein the recombinant protein further comprises truncation of at least one amino acid residue of N-terminus and at least one amino acid residue of C-terminus when compared to an amino acid sequence of a wild human PH20.

* * * * *

SEQUENCE LISTING

<160> NUMBER OF SEQ ID NOS: 2

<210> SEQ ID NO 1
<211> LENGTH: 442
<212> TYPE: PRT
<213> ORGANISM: Artificial Sequence
<220> FEATURE:
<223> OTHER INFORMATION: Synthetic construct

<400> SEQUENCE: 1

```
Leu Asp Phe Arg Ala Pro Pro Leu Ile Ser Asn Thr Ser Phe Leu Trp
1               5                   10                  15

Ala Trp Asn Ala Pro Ala Glu Arg Cys Val Lys Ile Phe Lys Leu Pro
            20                  25                  30

Pro Asp Leu Arg Leu Phe Ser Val Lys Gly Ser Pro Gln Lys Ser Ala
        35                  40                  45

Thr Gly Gln Phe Ile Thr Leu Phe Tyr Ala Asp Arg Leu Gly Tyr Tyr
    50                  55                  60

Pro His Ile Asp Glu Lys Thr Gly Asn Thr Val Tyr Gly Gly Ile Pro
65                  70                  75                  80

Gln Leu Gly Asn Leu Lys Asn His Leu Glu Lys Ala Lys Lys Asp Ile
                85                  90                  95

Ala Tyr Tyr Ile Pro Asn Asp Ser Val Gly Leu Ala Val Ile Asp Trp
            100                 105                 110

Glu Asn Trp Arg Pro Thr Trp Ala Arg Asn Trp Lys Pro Lys Asp Val
        115                 120                 125

Tyr Arg Asp Glu Ser Val Glu Leu Val Leu Gln Lys Asn Pro Gln Leu
    130                 135                 140

Ser Phe Pro Glu Ala Ser Lys Ile Ala Lys Val Asp Phe Glu Thr Ala
145                 150                 155                 160

Gly Lys Ser Phe Met Gln Glu Thr Leu Lys Leu Gly Lys Leu Leu Arg
                165                 170                 175

Pro Asn His Leu Trp Gly Tyr Tyr Leu Phe Pro Asp Cys Tyr Asn His
            180                 185                 190

Asn Tyr Asn Gln Pro Thr Tyr Asn Gly Asn Cys Ser Asp Leu Glu Lys
        195                 200                 205

Arg Arg Asn Asp Asp Leu Asp Trp Leu Trp Lys Glu Ser Thr Ala Leu
    210                 215                 220

Phe Pro Ser Val Tyr Leu Asn Ile Lys Leu Lys Ser Thr Pro Lys Ala
225                 230                 235                 240

Ala Phe Tyr Val Arg Asn Arg Val Gln Glu Ala Ile Arg Leu Ser Lys
                245                 250                 255

Ile Ala Ser Val Glu Ser Pro Leu Pro Val Phe Val Tyr His Arg Pro
            260                 265                 270

Val Phe Thr Asp Gly Ser Ser Thr Tyr Leu Ser Gln Gly Asp Leu Val
        275                 280                 285

Asn Ser Val Gly Glu Ile Val Ala Leu Gly Ala Ser Gly Ile Ile Met
    290                 295                 300

Trp Gly Ser Leu Asn Leu Ser Leu Thr Met Gln Ser Cys Met Asn Leu
305                 310                 315                 320

Gly Asn Tyr Leu Asn Thr Thr Leu Asn Pro Tyr Ile Ile Asn Val Thr
                325                 330                 335

Leu Ala Ala Lys Met Cys Ser Gln Val Leu Cys His Asp Glu Gly Val
            340                 345                 350

Cys Thr Arg Lys Gln Trp Asn Ser Ser Asp Tyr Leu His Leu Asn Pro
```

```
              355                 360                 365
Met Asn Phe Ala Ile Gln Thr Gly Lys Gly Gly Lys Tyr Thr Val Pro
        370                 375                 380

Gly Lys Val Thr Leu Glu Asp Leu Gln Thr Phe Ser Asp Lys Phe Tyr
385                 390                 395                 400

Cys Ser Cys Tyr Ala Asn Ile Asn Cys Lys Arg Val Asp Ile Lys
                405                 410                 415

Asn Val His Ser Val Asn Val Cys Met Ala Glu Asp Ile Cys Ile Glu
                420                 425                 430

Gly Pro Val Lys Leu Gln Pro Ser Asp His
            435                 440

<210> SEQ ID NO 2
<211> LENGTH: 447
<212> TYPE: PRT
<213> ORGANISM: Artificial Sequence
<220> FEATURE:
<223> OTHER INFORMATION: Synthetic construct

<400> SEQUENCE: 2

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Val
        35                  40                  45

Thr Gly Gln Asp Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Ile
        115                 120                 125

Tyr Lys Asn Arg Ser Ile Glu Leu Val Gln Gln Asn Val Gln Leu
    130                 135                 140

Asn Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Val Tyr Thr Arg Ile Val
            260                 265                 270

Phe Thr Asp Gln Val Leu Lys Phe Leu Ser Gln Asp Glu Leu Val Tyr
```

-continued

```
            275                 280                 285
Thr Phe Gly Glu Thr Val Ala Leu Gly Ala Ser Gly Ile Val Ile Trp
        290                 295                 300
Gly Thr Leu Ser Ile Met Arg Ser Met Lys Ser Cys Leu Leu Leu Asp
305                 310                 315                 320
Asn Tyr Met Glu Thr Ile Leu Asn Pro Tyr Ile Ile Asn Val Thr Leu
                325                 330                 335
Ala Ala Lys Met Cys Ser Gln Val Leu Cys Gln Glu Gln Gly Val Cys
            340                 345                 350
Ile Arg Lys Asn Trp Asn Ser Ser Asp Tyr Leu His Leu Asn Pro Asp
        355                 360                 365
Asn Phe Ala Ile Gln Leu Glu Lys Gly Gly Lys Phe Thr Val Arg Gly
    370                 375                 380
Lys Pro Thr Leu Glu Asp Leu Glu Gln Phe Ser Glu Lys Phe Tyr Cys
385                 390                 395                 400
Ser Cys Tyr Ser Thr Leu Ser Cys Lys Glu Lys Ala Asp Val Lys Asp
                405                 410                 415
Thr Asp Ala Val Asp Val Cys Ile Ala Asp Gly Val Cys Ile Asp Ala
            420                 425                 430
Phe Leu Lys Pro Pro Met Glu Thr Glu Glu Ser Gln Ile Phe Tyr
        435                 440                 445
```